US008883746B2

(12) United States Patent
Kang et al.

(10) Patent No.: US 8,883,746 B2
(45) Date of Patent: Nov. 11, 2014

(54) α-GALACTOSYLCERAMIDE DERIVATIVES, PHARMACEUTICALLY ACCEPTABLE SALTS THEREOF, PREPARATION METHOD AND PHARMACEUTICAL COMPOSITION FOR THE IMMUNE ADJUVANT CONTAINING THE SAME AS AN ACTIVE INGREDIENT

(75) Inventors: Chang-Yuil Kang, Seoul (KR); SangHee Kim, Seoul (KR); Hyun-Jun Youn, Seoul (KR); Yoon-Sook Lee, Yeosu-si (KR); Kyoo-A Lee, Gyeongju-si (KR); Taeho Lee, Seoul (KR); Dong Jae Baek, Seoul (KR); Minjae Cho, Eujungbu-si (KR)

(73) Assignee: SNU R&DB Foundation, Seoul (KR)

( * ) Notice: Subject to any disclaimer, the term of this patent is extended or adjusted under 35 U.S.C. 154(b) by 957 days.

(21) Appl. No.: 12/521,487

(22) PCT Filed: Dec. 27, 2007

(86) PCT No.: PCT/KR2007/006889
§ 371 (c)(1),
(2), (4) Date: Jun. 26, 2009

(87) PCT Pub. No.: WO2008/082156
PCT Pub. Date: Jul. 10, 2008

(65) Prior Publication Data
US 2010/0104590 A1    Apr. 29, 2010

(30) Foreign Application Priority Data

Dec. 30, 2006    (KR) .................. 10-2006-0139200

(51) Int. Cl.
*A61K 31/7028* (2006.01)
*A61K 31/00* (2006.01)
*C07H 15/04* (2006.01)
*C07H 15/00* (2006.01)

(52) U.S. Cl.
CPC ..................................... *C07H 15/00* (2013.01)
USPC ................ 514/25; 536/17.9; 536/4.1; 536/53

(58) Field of Classification Search
USPC ............................... 514/25; 536/17.9, 4.1, 53
See application file for complete search history.

(56) References Cited

U.S. PATENT DOCUMENTS

| 5,936,076 A | 8/1999 | Higa et al. |
| 2004/0127429 A1 | 7/2004 | Tsuji |

FOREIGN PATENT DOCUMENTS

| WO | WO 85/05031 | * 11/1985 |
| WO | WO 98/44928 | 10/1998 |
| WO | WO2006/026389 | 3/2006 |

OTHER PUBLICATIONS

Lee et al. (J. Med. Chem. 2007, 50, 585-589).*
Sakai et al. (Org. Lett., vol. 1, No. 3, 1999, 359-361).*
Faroux-Corlay, B. et al. "Amphiphilic Anionic Analogues of Galactosylceramide: Synthesis, Anti-HIV-1 Activity, and gp120 Binding"; (2001) *J. Med. Chem.* 44:2188-2203.
Kolb, HC et al. "The growing impact of click chemistry on drug discovery"; (2003) *Drug Discovery Today* 8:1128-1237.
Kolb, HC et al. "Click Chemistry: Diverse Chemical Function from a Few Good Reactions"; (2001) *Agnew. Chem. Int. Ed.* 40:2005-2021.
Savage, PB, et al. "Glycolipids for natural killer T cells"; (2006) *Chem. Soc. Rev.* 35:771-779.
Villard, R. et al. "Asymmetric Synthesis of Water-Soluble Analogues of Galactosylceramide, an HIV-1 Receptor: New Tools to Study Virus—Glycolipid Interactions"; (2002) *Chem.Bio.Chem.*3:517-525.
Annual. Review Immune. (2003), pp. 71-77—In Japenese, English summary of article provided.
Cottard et al. (2000) "Adeno-Associated Virus-Mediated Delivery of IL-4 Prevents Collagen-Induced Arthritis," Gene Therapy 7:1930-1939.
Hunt et al. (2000) "Cytokine Gene Polymorphisms in Autoimmune Thyroid Disease," The Journal of Clinical Endocrinology & Metabolism, 85(5):1984-1988.
Joyce (2000) "Natural T cells: Cranking up the immune system by prompt cytokine secretion," PNAS, 97(13): 6933-6935.
Kawano et al. (1997) "CD1d-Restricted and TCR-Mediated Activation of $V_\alpha 14$ NKT Cells by Glycosylceramides," Science 278:1626-1629.
Miyake et al. (2005) "Therapeutic Potential og Glycolipid Ligands for Natural Killer (NK) T Cells in the Suppression of Autoimmune Diseases," Curr Drug Targets Immune Endocr Metabol Disord 5(3):315-322. (Abstract only).
Miyamoto et al. (2001) "A Synthetic Glycolipid Prevents Autoimmune Encephalomyelitis By Inducing $T_H2$ Bias of Natural Killer T Cells," Nature 413:531-534.
Mizuno et al. (2004) "Synthetic Glycolipid OCH Prevents Insulitis and Diabetes in NOD Mice," J Autoimmunity 23:293-300.
Natori et al. (1993) "Agelasphins, Novel α-Galactosylceramides from the Marine Sponge *Agelas mauritianus*," Tetrahedron Letters 34(35):5591-5592.
Natori et al. (1994) "Agelasphins, Novel Antitumor and Immunostimulatory Cerebrosides from the Marine Sponge *Agelas mauritianus*," Tetrahedron 50(9):2771-2784.
Oki et al. (Jun. 2004) "The Clinical Implication and Molecular Mechanism of Preferential IL-4 Production by Modified Glycolipid-Stimulated NKT Cells," J Clinical Investigation 113(11):1631-1640.
Zamorano et al. (2003) "Interleukin-4: A multifunctional cytokine," Inmunología, 22(2):215-224.

* cited by examiner

*Primary Examiner* — Shaojia Anna Jiang
*Assistant Examiner* — Michael C Henry
(74) *Attorney, Agent, or Firm* — Lathrop & Gage LLP

(57) ABSTRACT

Disclosed are novel α-galactosylceramide derivatives, pharmaceutically acceptable salts thereof, preparation methods thereof, and pharmaceutical compositions for use in an immune adjuvant containing the same as an active ingredient. The derivatives, in which the amide moiety of α-GalCer is bioisosterically replaced with a triazole moiety, direct cytokine secretion toward IL-4 rather than IFN-γ and thus can be used as a therapeutic for autoimmune diseases regulated by IL-4, such as type 1 diabetes and multiple sclerosis.

19 Claims, 5 Drawing Sheets

(a)

(b)

α-GALACTOSYLCERAMIDE DERIVATIVES, PHARMACEUTICALLY ACCEPTABLE SALTS THEREOF, PREPARATION METHOD AND PHARMACEUTICAL COMPOSITION FOR THE IMMUNE ADJUVANT CONTAINING THE SAME AS AN ACTIVE INGREDIENT

CROSS-REFERENCE TO RELATED APPLICATIONS

This application is the U. S. National Stage of International Application No. PCT/KR2007/006889, filed Dec. 27, 2007 and published in English on Jul. 10, 2008 as WO 2008/082156, which claims priority to South Korean application 10-2006-0139200, filed Dec. 30, 2006, all of which are hereby incorporated by reference in their entirety to the extent not inconsistent with the disclosure herein.

TECHNICAL FIELD

The present invention relates to α-galactosylceramide derivatives, pharmaceutically acceptable salts thereof, preparation methods thereof, and pharmaceutical compositions for use in immune adjuvants containing the same as an active ingredient. More particularly, the present invention relates to α-galactosylceramide derivatives capable of directing cytokine release toward IL-4 rather than IFN-γ, thereby being useful in the treatment of IL-4 regulated autoimmune diseases, such as type 1 diabetes and multiple sclerosis, pharmaceutically acceptable salts thereof, preparation methods thereof, and pharmaceutical compositions for use in immune adjuvants containing the same as an active ingredient.

BACKGROUND ART

Natural killer T (NKT) cells are a subset of T cells that co-express an αβ T cell receptor (TCR), but also express a variety of molecular markers that are typically associated with NK cells. They differ from conventional αβ T cells in that the diversity of their TCRs is much more limited and in that they recognize lipids and glycolipids presented by the major histocompatibility complex (MHC)-like molecules, such as CD1d molecules, part of the CD1 family of antigen presenting molecules, rather than peptide-MHC complexes (Brigl, M et al., Annu. Rev. Immunol., 22:817-890, 2004). NKT cells are stimulated by APC via CD1d-TCR interactions and rapidly produce many predominantly Th1 or Th2 type cytokines, such as interferon-γ (IFN-γ, Th1) and interleukin-4 (IL-4, Th2), which play an important role in the activation of the cells responsible for innate and adaptive immune responses. The balance of Th1/Th2 cytokine responses is known to play an important role in orchestrating immune response properties (Chen et al., J. Immunol., 159: 2240, 1997; Wilson et al., Proc. Natl. Acad. Sci. U.S.A., 100: 10913, 2003).

α-Galactosylceramide (α-GalCer), a structurally modified derivative of the extract agelasphin from marine sponges, was first discovered as a ligand for the Vα14+ T cell receptor of NKT (natural killer T cell) and shows highly potent activity (Morita, M. et al., J. Med. Chem. 38:2176-2187, 1995). Since the discovery thereof, α-GalCer has been most widely studied in the context of the biological and pharmaceutical properties of NKT cells. Many derivatives thereof have been synthesized and evaluated for structure-activity relationship (SAR) (Savage, P., et al., Chem. Soc. Rev., 35:771-779, 2006). SAR studies on the sugar moiety of α-GalCer revealed that the galactosyl group plays an important role in the activation of NKT cells through an α-GalCer/CD1d/TCR interaction. The α-anomeric linkage structure was found to completely allow α-GalCer to act as a potent and effective ligand for NKT cells (Kawano, T. et al., Science, 278:1626-1629, 1997). Also, it was reported that, whereas the hydroxide group at position 2 of the sugar moiety is most responsible for the recognition of NKT cells through TCR, chemical modification can be applied to the hydroxide groups at positions 3 and 6 (Barbieri, L. et al., Eur. J. Org. Chem., 468-473, 2004).

Modifications in fatty acid chains as well as in the sphingosine moiety are likely to bring about a change in the stability of the glycolipid-CD1d complex, thus having an influence on cytokine secretion. For example, PBS-25, an α-GalCer variant with a shorter fatty acid chain, induces the secretion of a greater amount of Th2-cytokines, compared to α-GalCer (Goff, R. D. et al., J. Am. Chem. Soc., 126:13602-13603, 2004). The removal of 9 carbons from the fatty acid chain of phytosphingosine increases the relative amounts of Th2-cytokine release by NKT cells (Miyamoto, K. et al., Nature, 413:531-534, 2001) and the presence of an aromatic ring in the fatty acid chain results in an increase in Th1 cytokine secretion (Fujio, M. et al., J. Am. Chem. Soc., 128:9022-9023, 2006). Interestingly, the substitution of the oxygen atom at the anomer position of α-GalCer with $CH_2$ changes the pattern of cytokine secretion. An animal test showed that these C-glycoside analogs to α-GalCer can strongly induce the secretion of Th1-cytokines in NKT cells (Frank, R. W. et al., Acc. Chem. Res., 39:692-701, 2006).

The SAR of α-GalCer has recently been identified through the X-ray crystallographic structure of an α-GalCer-CD1d complex (Zajonc, D. M. et al., Nat. Immunol., 6:810-818, 2005), which shows the accurate fit of the α-GalCer fatty acid chain into the two hydrophobic grooves of CD1d. Hydrogen bonds between the surface residues of CD1d and the hydroxide groups of galactose and sphingoshine are believed to play a critical role in maintaining the accurate position and direction of α-GalCer necessary for TCR recognition. The crystalline structure of the complex of human CD1d and α-GalCer demonstrated that the amide group of α-GalCer does not form a hydrogen bond with the surface residues of CD1d (Koch, M. et al., Nat. Immunol., 6:819-826, 2005). In the crystalline structure of the complex of murine CD1d and PBS-25, the NH of the PBS-25 amide is seen to form a hydrogen bond with the α2 spiral structure of CD1d, but the carbonyl group of the amide does not, indicating that the amide group of α-GalCer may be a recognition target in contact with the TCR of NKT cells, in addition to playing a structural role in determining the three-dimensional position of the fatty acid chain.

The α-GalCer variants reported thus far can be divided into three groups: modifications in sphingosine moiety; fatty acid chain; and sugar moiety. Nowhere have partial modifications in the amide moiety of α-GalCer been reported before the present invention. Because the amide group acts to form a hydrogen bond at a binding position, the bioisosteric replacement of the α-GalCer amide moiety can provide interesting information about the biological features of NKT cells. Thanks to the different electronic and steric properties of isosteres, modification of the amide moiety results in a change in the stability of glycolipid-CD1d complex and the position of the sugar head in the binding grooves, leading to the possibility of developing galactosylceramide having more potent antigenicity. Furthermore, the bioisosteric replacement is expected to have an influence on the metabolism of α-GalCer, thus leading to a change in immune response.

Among a variety of bioisosteres of the amide moiety, 1,2,3-triazole compounds have gained increasing attention in drug discovery since the introduction of "Click" chemistry by Sharpless (Kolb, H. C. et al., Drug Discov. Today, 8:1128-1237, 2003, Kolb, H. C., et al., Angew. Chem. Int. Ed., 40:2004-2021, 2001). 1,2,3-Triazole compounds can mimic the topological and electronic features of an amide bond, providing a firm binding unit. These compounds can actively participate in hydrogen bonding and dipole-dipole interactions, thanks to the strong dipole moment. Compared to other amide compounds, however, triazole compounds are surprisingly stable to hydrolysis and in oxidation and reduction conditions. Nowhere has the introduction of 1,2,3-triazole into the ceramide moiety been reported, thus far.

Leading to the present invention, intensive and thorough research into pharmaceutically effective modified α-GalCer derivatives, conducted by the present inventors, resulted in the finding that the bioisosteric replacement of the amide moiety of α-GalCer with triazole of various fatty acid chain lengths, based on the crystal structure of a CD1d-α-GalCer complex, increases the IL-4 vs. IFN-γ bias of released cytokines.

DISCLOSURE

Technical Problem

Accordingly, it is an object of the present invention to provide a novel α-galactosylceramide derivative, a pharmaceutically acceptable derivative, a method for preparing the same, and a pharmaceutical composition for use in an immune adjuvant, containing the same as an active ingredient.

Technical Solution

In order to accomplish the above objects, the present invention provides a novel α-galactosylceramide derivative, a pharmaceutically acceptable derivative, a method for preparing the same, and a pharmaceutical composition for use in an immune adjuvant, containing the same as an active ingredient.

Advantageous Effects

The bioisosteric replacement of the amide moiety of α-GalCer with triazole directs the cytokine secretion toward IL-4 rather than IFN-γ, and thus, the compounds of the present invention can be used as an effective therapeutic for IL-4-regulated autoimmune diseases, such as type 1 diabetes and multiple sclerosis.

BEST MODE

Figure 1:
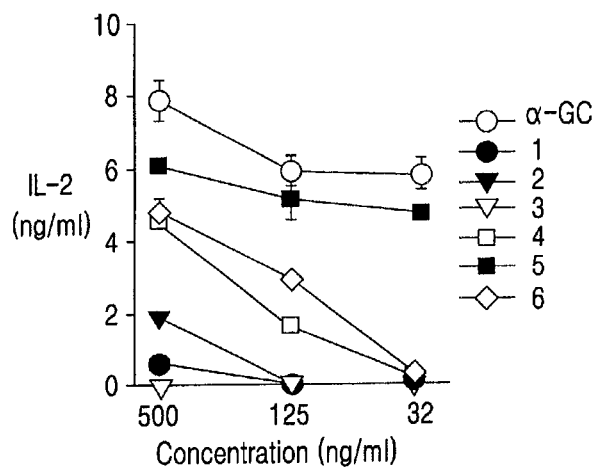
FIG. 1 shows stimulatory effects of the parent compound α-GalCer and the compounds of the present invention on NKT hybridoma cells.
Figure 1:
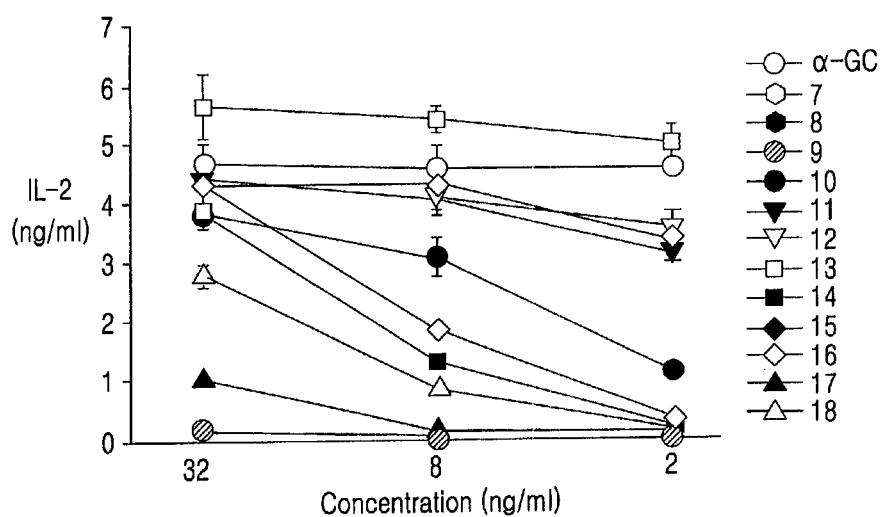

In accordance with an aspect thereof, the present invention pertains to a novel alpha-galactosylceramide derivative represented by the following Chemical Formula 1.

[Chemical Formula 1]

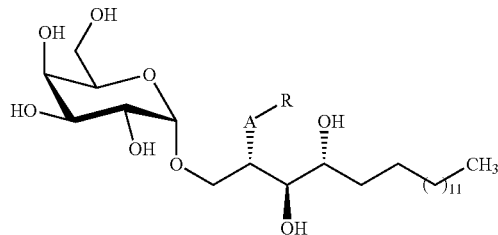

wherein,
A is a triazole group

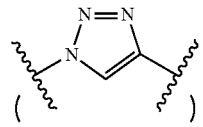

or an amide group

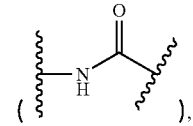

and
R is an alkyl group of $C_1$~$C_{35}$ without any substituent, or with at least one substituent when A is a triazole group, said substituent being halogen, hydroxy, amino, amino having one or more alkyl groups of $C_1$~$C_{20}$, thiol, cyano, nitro, sulfonyl, phenyl, alkoxy of $C_1$~$C_{30}$, alkyl of $C_1$~$C_{30}$, haloalkyl of $C_1$~$C_{30}$, hydroxyalkyl of $C_1$~$C_{30}$, alkoxyalkyl of $C_1$~$C_{30}$, aryl of $C_5$~$C_{10}$, heteroaryl of $C_5$~$C_{10}$, arylalkyl of $C_5$~$C_{10}$ or heteroarylalkyl of $C_5$~$C_{10}$; or R is an alkyl group of $C_1$~$C_{35}$ with at least one substituent when A is an amide group, said substituent being halogen, hydroxy, amino, amino having one or more alkyl groups of $C_1$~$C_{20}$, thiol, cyano, nitro, sulfonyl, phenyl, alkoxy of $C_1$~$C_{30}$, alkyl of $C_1$~$C_{30}$, haloalkyl of $C_1$~$C_{30}$, hydroxyalkyl of $C_1$~$C_{30}$ alkoxyalkyl of $C_1$~$C_{30}$, aryl of $C_5$~$C_{10}$, heteroaryl of $C_5$~$C_{10}$, arylalkyl of $C_5$~$C_{10}$ or heteroarylalkyl of $C_5$~$C_{10}$.

Preferably, A is a triazole group or an amide group, and R is an alkyl of $C_1$~$C_{30}$ without any substituent, or with at least one substituent when A is a triazole group, said substituent being halogen, hydroxy, amino, amino having one or more alkyl groups of $C_1$~$C_{15}$, thiol, cyano, nitro, sulfonyl, phenyl, alkoxy of $C_1$~$C_{20}$, alkyl of $C_1$~$C_{20}$, haloalkyl of $C_1$~$C_{20}$, hydroxyalkyl of $C_1$~$C_{20}$, alkoxyalkyl of $C_1$~$C_{20}$, aryl of $C_5$~$C_8$, heteroaryl of $C_5$~$C_8$, arylalkyl of $C_5$~$C_8$ or heteroarylalkyl of $C_5$~$C_8$, or R is an alkyl group of $C_1$~$C_{30}$ with at least one substituent when A is an amide group, said substituent being a halogen, hydroxy, amino, amino having one or more alkyl groups of $C_1$~$C_{15}$, thiol, cyano, nitro, sulfonyl, phenyl, alkoxy of $C_1$~$C_{20}$, alkyl of $C_1$~$C_{20}$, haloalkyl of $C_1$~$C_{20}$, hydroxyalkyl of $C_1$~$C_{20}$ alkoxyalkyl of $C_1$~$C_{20}$, aryl of $C_5$~$C_8$, heteroaryl of $C_5$~$C_8$, arylalkyl of $C_5$~$C_8$ or heteroarylalkyl of $C_5$~$C_8$.

More preferably, A is a triazole group or an amide group, and R is an alkyl of $C_1$~$C_{25}$ without any substituent, or with at least one substituent when A is a triazole group, said substituent being halogen, hydroxy, amino, amino having one or more alkyl groups of $C_1$~$C_{10}$, thiol, phenyl, alkyl of $C_1$~$C_{20}$, haloalkyl of $C_1$~$C_{20}$, or hydroxyalkyl of $C_1$~$C_{20}$, or R is an alkyl group of $C_1$~$C_{25}$ with at least one substituent when A is an amide group, said substituent being a halogen, hydroxy, amino, amino having one or more alkyl groups of $C_1$~$C_{10}$, thiol, phenyl, alkyl of $C_1$~$C_{20}$, haloalkyl of $C_1$~$C_{20}$, or hydroxyalkyl of $C_1$~$C_{20}$.

More preferably, A is a triazole group or an amide group, and R is an alkyl of $C_1$~$C_{25}$ without any substituent, or with at least one substituent when A is a triazole group, said substituent being phenyl, or R is an alkyl group of $C_1$~$C_{25}$ with at least one substituent when A is an amide group, said substituent being a halogen, hydroxy, amino, thiol, or amino having one or more alkyl groups of $C_1$~$C_7$.

As used herein with regard to the derivative of Chemical Formula 1, the term "alkyl" is intended to include straight or branched alkyl groups.

In the derivative of Chemical Formula 1, R is substituted at position 4 of the triazole group or at the carbonyl carbon of the amide group.

Concrete examples of the novel alpha-galactosylceramide derivative represented by Chemical Formula 1 include:

1) (2S,3R,4S,5R)-2-((2S,3S,4R)-2-(4-hexyl-1H-1,2,3-triazol-1-yl)-3,4-dihydroxyoctadecyloxy)-6-(hydroxymethyl)-tetrahydro-2H-pyrane-3,4,5-triol;
2) (2S,3R,4S,5R)-2-((2S,3S,4R)-2-(4-heptyl-1H-1,2,3-triazol-1-yl)-3,4-dihydroxyoctadecyloxy)-6-(hydroxymethyl)-tetrahydro-2H-pyrane-3,4,5-triol;
3) (2S,3R,4S,5R)-2-((2S,3S,4R)-2-(4-hexadecyl-1H-1,2,3-triazol-1-yl)-3,4-dihydroxyoctadecyloxy)-6-(hydroxymethyl)-tetrahydro-2H-pyrane-3,4,5-triol;
4) (2S,3R,4S,5R)-2-((2S,3S,4R)-3,4-dihydroxy-2-(4-tricosyl-1H-1,2,3-triazol-1-yl)octadecyloxy)-6-(hydroxymethyl)-tetrahydro-2H-pyrane-3,4,5-triol;
5) (2S,3R,4S,5R)-2-((2S,3S,4R)-3,4-dihydroxy-2-(4-tetracosyl-1H-1,2,3-triazol-1-yl)octadecyloxy)-6-(hydroxymethyl)-tetrahydro-2H-pyrane-3,4,5-triol;
6) (2S,3R,4S,5R)-2-((2S,3S,4R)-3,4-dihydroxy-2-(4-pentacosyl-1H-1,2,3-triazol-1-yl)octadecyloxy)-6-(hydroxymethyl)-tetrahydro-2H-pyrane-3,4,5-triol;
7) (2S,3R,4S,5R)-2-((2S,3S,4R)-3,4-dihydroxy-2-(4-(6-phenylhexyl)-1H-1,2,3-triazol-1-yl)octadecyloxy)-6-(hydroxymethyl)-tetrahydro-2H-pyrane-3,4,5-triol;
8) (2S,3R,4S,5R)-2-((2S,3S,4R)-3,4-dihydroxy-2-(4-(7-phenylheptyl)-1H-1,2,3-triazol-1-yl)octadecyloxy)-6-(hydroxymethyl)-tetrahydro-2H-pyrane-3,4,5-triol;
9) (2S,3R,4S,5R)-2-((2S,3S,4R)-3,4-dihydroxy-2-(4-(8-phenyloctyl)-1H-1,2,3-triazol-1-yl)octadecyloxy)-6-(hydroxymethyl)-tetrahydro-2H-pyrane-3,4,5-triol;
10) 11-amino-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)undecanamide;
11) 12-amino-N-((2S,3S,4R)-3,4-dihydroxy-1-((2S,3R,4S,5R)-3,4,5-trihydroxy-6-(hydroxymethyl)-tetrahydro-2H-pyran-2-oxy)octadecan-2-yl)dodecanamide;
12) N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-hydroxyundecanamide;
13) N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-12-hydroxydodecanamide;
14) 8-(diheptylamino)-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)octanamide;
15) N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-(dipentylamino)undecanamide;
16) 11-(diheptylamino)-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)undecanamide;
17) N-((2S,3S,4R)-3,4-dihydroxy-1-((2S,3R,4S,5R)-3,4,5-trihydroxy-6-(hydroxymethyl)-tetranydro-2H-pyran-2-yloxy)octadecan-2-yl)-11-mercaptoundecanamide; and
18) N-((2S,3S,4R)-3,4-dihydroxy-1-((2S,3R,4S,5R)-3,4,5-dihydroxy-6-(hydroxymethyl)-tetrahydro-2H-pyran-2-yloxy)octadecan-2-yl)-12-mercaptododecanamide, The novel alpha-galactosylceramide derivative of Chemical Formula 1 may be prepared via an intermediate the concrete examples of which include:

19) 1-((2S,3S,4R)-3,4-bis(4-methoxybenzyloxy)-1-((2S,3R,4S,5S)-3,4,5-tris(benzyloxy)-6-(benzyloxymethyl)-tetranydro-2H-pyran-2-yloxy)octadecan-2-yl)-4-hexyl-1H-1,2,3-triazole;
20) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-heptyl-1H-1,2,3-triazole;
21) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-hexadecyl-1H-1,2,3-triazole;
22) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-tricosyl-1H-1,2,3-triazole;
23) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-tetracosyl-1H-1,2,3-triazole;
24) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-pentacosyl-1H-1,2,3-triazole;
25) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(6-phenylhexyl)-1H-1,2,3-triazole;
26) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(7-phenylheptyl)-1H-1,2,3-triazole;
27) 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(8-phenyloctyl)-1H-1,2,3-triazole;
28) benzyl (13S,14S,15R)-14,15-bis(4-methoxybenzyloxy)-11-oxo-13-(((2S,3R,4S,5S)-3,4,5-tris(benzyloxy)-6-(benzyloxymethyl)-tetrahydro-2H-pyran-2-yloxy)methyl) nonacosylcarbamate(google=0!);
29) benzyl (14S,15S,16R)-15,16-bis(4-methoxybenzyloxy)-12-oxo-14-(((2S,3R,4S,5S)-3,4,5-tris(benzyloxy)-6-(benzyloxymethyl)-tetrahydro-2H-pyran-2-yloxy)methyl)triacontyl carbamate;

30) (13S,14S,15R)-1-(benzyloxy)-14,15-bis(4-methoxybenzyloxy)-13-(((2S,3R,4S,5S)-3,4,5-tris(benzyloxy)-6-(benzyloxymethyl)-tetrahydro-2H-pyran-2-yloxy)methyl)nonacosan-11-one;
31) (14S,15S,16R)-1-(benzyloxy)-15,16-bis(4-methoxybenzyloxy)-14-(((2S,3R,4S,5S)-3,4,5-tris(benzyloxy)-6-(benzyloxymethyl)-tetrahydro-2H-pyran-2-yloxy)methyl)triacontan-12-one;
32) N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-8-(diheptylamino)octanamide;
33) N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-11-(dipentylamino)undecanamide;
34) N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-11-(diheptylamino)undecanamide;
35) (13S,14S,15R)-1-bromo-14,15-bis(4-methoxybenzyloxy)-13-M2S,3R,4S,5S)-3,4,5-tris(benzyloxy)-6-(benzyloxymethyl)-tetrahydro-2H-pyran-2-yloxy)methyl)nonacosan-11-one;
36) (14S,15S,16R)-1-bromo-15,16-bis(4-methoxybenzyloxy)-14-(((2S,3R,4S,5S)-3,4,5-tris(benzyloxy)-6-(benzyloxymethyl)-tetrahydro-2H-pyran-2-yloxy)methyl)triacontan-12-one;
37) (13S,14S,15R)-1-mercapto-14,15-bis(4-methoxybenzyloxy)-13-M2S,3R,4S,5S)-3,4,5-tris(benzyloxy)-6-(benzyloxymethyl)-tetrahydro-2H-pyran-2-yloxy)methyl)nonacosan-11-one; and
38) (14S,15S,16R)-1-mercapto-15,16-bis(4-methoxybenzyloxy)-14-M2S,3R,4S,5S)-3,4,5-tris(benzyloxy)-6-(benzyloxymethyl)-tetrahydro-2H-pyran-2-yloxy)methyl)triacontan-12-one.

The novel alpha-galactosylceramide derivative of Chemical Formula 1 may be in the form of any salt, whether pharmaceutically acceptable or not, in accordance with the present invention. Within the range of pharmaceutically acceptable salts are included acid addition salts formed with pharmaceutically or physiologically acceptable organic or inorganic acids. Useful as the free organic acids are carboxylic acid, phosphoric acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methyl sulfate, ethyl sulfate, and dodecyl sulfate. Examples of inorganic acids suitable for use in the present invention include hydrochloric acid, sulfuric acid, bromic acid, sulfurous acid, and phosphoric acid.

Also, hydrates and solvates of the novel alpha-galactosylceramide derivative of Chemical Formula 1 according to the present invention fall within the scope of the present invention.

In accordance with another aspect thereof, the present invention pertains to a method for preparing the novel alpha-galactosylceramide of Chemical Formula 1.

The method, as illustrated in the following Reaction scheme 1, comprises:
reacting a compound of Chemical Formula 2 with an alkyne compound to afford an intermediate of Chemical Formula 4 (step 1); and
deprotecting the intermediate with Pd(OH)$_2$ (step 2).

[Reaction Scheme 1]

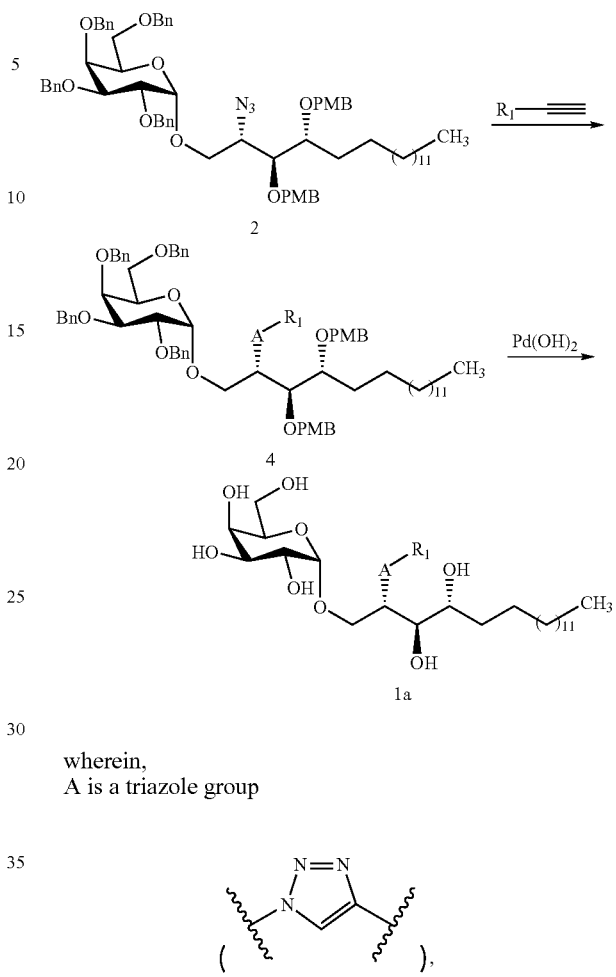

wherein,
A is a triazole group

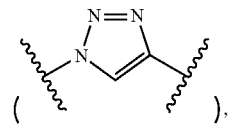

$R_1$ is the R defined in Chemical Formula 1, and
Bn and PMB represent benzyl and p-methoxybenzyl, respectively.

The method will be further elucidated in a stepwise manner.

In step 1, the starting material of Chemical Formula 2 is reacted with an alkyne compound to afford an intermediate according to Chemical Formula 4. The compound of Chemical Formula 2 is reacted with 1-alkyne in the presence of 1 M sodium ascorbate in a solvent mixture of 0.2-0.5 M t-butyl alcohol/water (1:1, v/v) at room temperature to synthesize the intermediate of Chemical Formula 4. Extraction with ethyl acetate, concentration, and silica gel column chromatography eluting with hexane/ethyl acetate yield the intermediate of Chemical Formula 4 in a pure form. The compound of Chemical Formula 2, galactosyl-azido-phytosphingosine, can be produced from commercially available D-ribo-phytosphingosine at high yield using a well-known 5-step synthesis method.

In step 2, the intermediate prepared in step 1 is reacted with Pd(OH)$_2$ to remove the protecting group. In a 0.01~0.1 M mixed solvent of ethyl alcohol/methylene chloride (3:1, v/v), the intermediate is reacted with Pd(OH)$_2$ at room temperature for 5~8 hrs in a hydrogen atmosphere (1 atm) to synthesize a deprotected α-galactosylceramide derivative. This can be purified through silica gel column chromatography eluting with hexane/ethylacetate.

Also, the present invention pertains to a method for preparing the novel alpha-galactosylceramide of Chemical Formula 1, as illustrated in the following Reaction Scheme 2, comprising:

reacting a compound of Chemical Formula 3 with a carboxylic acid compound to afford an intermediate of Chemical Formula 5 (step 1); and deprotecting the intermediate with Pd(OH)$_2$ (step 2).

[Reaction Scheme 2]

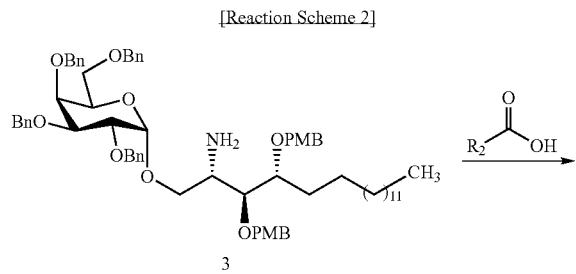

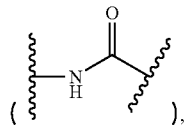

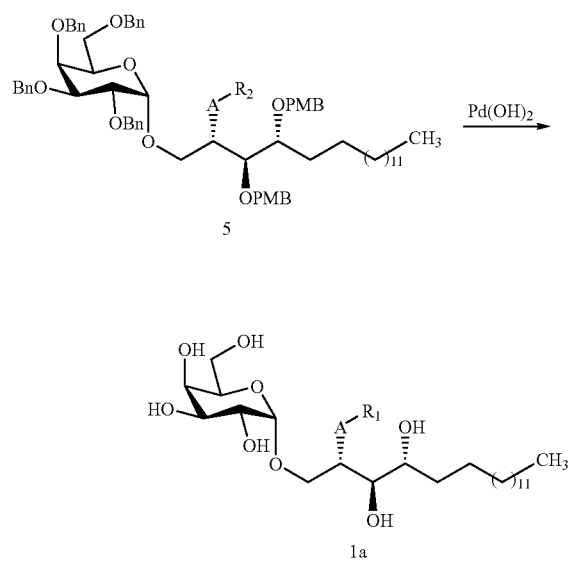

wherein,

A is an amide group $$\begin{matrix} \xi \\ \xi \end{matrix} -\underset{H}{N}-\overset{O}{\underset{\|}{C}}-\begin{matrix} \xi \\ \xi \end{matrix}$$

( ),

R$_1$ is the R defined in Chemical Formula 1,

R$_2$ is a substituent readily convertible to R$_1$, which is protected with a protecting group such as benzyloxycarbonyl (Cbz) or benzyl (Bn), and Bn and PMB represent benzyl and p-methoxybenzyl, respectively.

The method will be further elucidated in a stepwise manner.

In step 1, the starting material of Chemical Formula 3 is reacted with a carboxylic acid compound to afford an intermediate of Chemical Formula 5. The compound of Chemical Formula 3 is reacted with a carboxylic acid in the presence of N-(3-dimethylaminopropyl)-N'-ethylcarbodiimide hydrochloride and 4-dimethyl aminopyridine in 0.2-0.5 M methylene chloride solvent at room temperature to synthesize the intermediate of Chemical Formula 5. Silica gel column chromatography eluting with hexane/ethyl acetate gives the intermediate of Chemical Formula 5 in a pure form.

In step 2, the intermediate prepared in step 1 is deprotected through a reaction with Pd(OH)$_2$. In a 0.01~0.1 M mixed solvent of ethyl alcohol/methylene chloride (3:1, v/v), the intermediate is reacted with Pd(OH)$_2$ at room temperature for 5~8 hrs in a hydrogen atmosphere (1 atm) to synthesize a deprotected α-galactosylceramide derivative. This can be purified through silica gel column chromatography eluting with hexane/ethylacetate.

Also, the present invention pertains to a method for preparing the novel alpha-galactosylceramide of Chemical Formula 1, as illustrated in the following Reaction Scheme 3, comprising:

reacting a compound of Chemical Formula 3 with a carboxylic acid compound to afford an intermediate of Chemical Formula 7 (step 1);

reacting the intermediate of Chemical Formula 7 with a thiourea compound to form an intermediate of Chemical Formula 8, with a thiol group introduced thereinto (step 2); and deprotecting the intermediate with Pd(OH)$_2$ (step 2).

[Reaction Scheme 3]

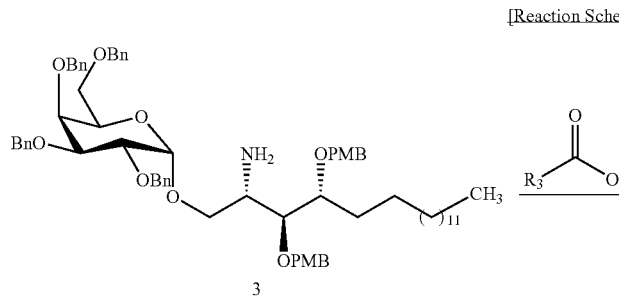

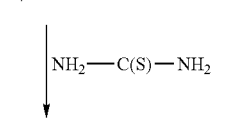

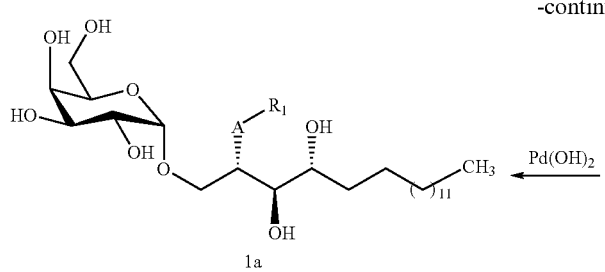

1a

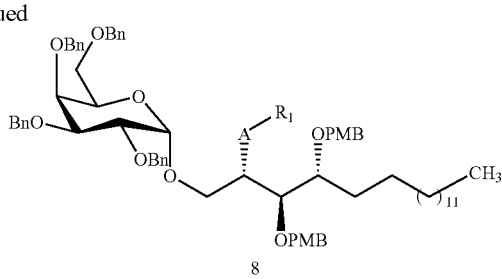

8 wherein,
A is an amide group

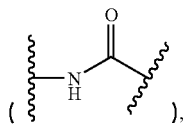

$R_1$ is the same R that is defined as having at least one thiol substituent in Chemical Formula 1, $R_3$ is a substituent readily convertible to $R_1$, which has a leaving group replaceable with a thiourea, such as halogen, and Bn and PMB are as defined in Reaction Scheme 1.

This method will be further elucidated in a stepwise manner.

In step 1, the starting material of Chemical Formula 3 is reacted with a carboxylic acid compound to afford an intermediate of Chemical Formula 7. The compound of Chemical Formula 3 is reacted with a carboxylic acid in the presence of bromic acid, N-(3-dimethylaminopropyl)-N'-ethylcarbodiimide hydrochloride and 4-dimethyl aminopyridine in a methylene chloride solvent at room temperature to synthesize the intermediate of Chemical Formula 5.

In step 2, a thiol group is introduced from thiourea into the intermediate of Chemical Formula 7 to give the intermediate of Chemical Formula 8. In detail, the intermediate of Chemical Formula 7 is fluxed for 2 hrs in a 0.2~0.5 M ethyl alcohol solvent, followed by the slow addition of 5 N sodium hydroxide to substitute the halogen of the intermediate of Chemical Formula 7, such as bromine, with a thiol group. Silica gel column chromatography eluting with hexane/ethyl acetate gives the intermediate of Chemical Formula 8 in a pure form.

In step 3, the intermediate of Chemical Formula 8, prepared in step 1, is deprotected by reaction with Pd(OH)$_2$. In a 0.01~0.1 M mixed solvent of ethyl alcohol/methylene:chloride (3:1, v/v), the intermediate is reacted with Pd(OH)$_2$ at room temperature for 5~8 hrs in a hydrogen atmosphere (1 atm) to synthesize a deprotected α-galactosylceramide derivative. This can be purified through silica gel column chromatography eluting with hexane/ethylacetate.

In accordance with a further aspect thereof, the present invention provides a cytokine secretion inhibitor, comprising the α-galactosylceramide derivative represented by Chemical Formula 1 or a pharmaceutically acceptable salt thereof as an active ingredient.

In accordance with still a further aspect thereof, the present invention provides a pharmaceutical composition for use as immune adjuvant, comprising the α-galactosylceramide derivative represented by Chemical Formula 1 or a pharmaceutically acceptable salt thereof as an active ingredient.

α-Galactosylceramide (α-GalCer), a structurally modified glycolipid obtained from marine sponges, is known to be a ligand for the Vα14+ T cell receptor of NKT (natural killer T cell) and to be presented by CD1d-expressing antigen presenting cell (APC) (Kawano et al., Science, 278: 1626, 1997). Once activated, NKT cells produce IFN-γ and IL-4 at high levels, regulating immune responses to specific diseases or infections (Chen et al., J. Immunol., 159: 2240, 1997; Wilson et al., Proc. Natl. Acad. Sci. U.S.A., 100: 10913, 2003).

In previous studies, the ability of α-GalCer was assessed with vaccines for systemic delivery. α-GalCer was reported to act as an effective adjuvant against infection (Gonzalez-Aseguinolaza et al., Proc. Natl. Acad. Sci. U.S.A., 97: 8461, 2000; Gonzalez-Aseguinoalza et al., J. Exp. Med., 195: 615, 2002), autoimmune diseases (Laloux et al., J. Immunol., 166: 3749, 2001: Teige et al., J. Immunol., 172: 186, 2004) and tumors (Hermans et al., J. Immunol., 171: 5140, 2003; Fujii et al., J. Exp. Med., 199: 1607, 2003; Hayakawa et al., Proc. Natl. Acad. Sci. U.S.A., 100: 9464, 2003).

Once stimulated, NKT hybridoma cell lines produce IL-2, whereas NKT cells produce various cytokines including IFN-γ (Th1) and IL-4 (Th2). Because the production ratio of Th1/Th2 cytokines, determined through biological antagonism and balance therebetween, plays an important role in orchestrating immune response properties (Pai, E. et al., J. Immunol., 166:662-668, 2001), NKT cell-enriched splenocytes are incubated with triazole 1~6 and the supernatant of the co-culture is quantified for IFN-γ and IL-4 (Fujii, S. et al., Nat. Immunol. 3:867-874, 2002) in the present invention.

As will be elucidated in Experimental Examples 1 to 3, the compounds having long fatty acid chains of Examples 4 to 6, 10 to 12, and 14 to 18, when used at high levels (100~500 ng/mL), are observed to allow the production of lower levels of IL-2 than does the mother compound α-GalCer (FIGS. 1a and 1b). Modified derivatives with the bioisosteric replacement of the amide moiety of α-GalCer with a triazole moiety are found to direct the cytokine secretion toward one of IL-4 and IFN-γ. In addition, the stimulatory effects of the derivatives of the present invention depend on the length of the fatty acid chains thereof. Particularly, α-galactosylceramide derivatives having long fatty acid chains show effects of inducing cytokine secretion as good as those achieved by α-GalCer, with induction preference for Th2 cytokine secretion over Th1 cytokine secretion.

Therefore, the α-galactosylceramide derivatives according to the present invention can be used as a cytokine secretion inhibitor useful in the treatment of autoimmune diseases, such as type 1 diabetes and multiple sclerosis or as an active agent of a pharmaceutical composition for use as an immune adjuvant effective in the treatment of autoimmune diseases.

The α-galactosylceramide derivative of Chemical Formula 1 according to the present invention may be administered via oral routes or non-oral routes, including mucous membrane, veins, muscles, etc. and may be provided in typical medicinal forms. It is usually formulated in combination with a diluent or excipient, such as a filler, a thickening agent, a binder, a wetting agent, a disintegrant, a surfactant, etc. Solid agents intended to be used for oral administration of the compound of the present invention may be in the form of tablets, pills, powders, granules, capsules, and the like. These solid agents are formulated in combination with at least one excipient, such as starch, calcium carbonate, sucrose, lactose, or gelatine. In addition, a lubricant, such as magnesium stearate, talc, or the like, may also be added. Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid agents for the oral administration of the compound of the present invention. Also, non-oral dosage forms of the compound of the present invention include sterile aqueous solutions, non-aqueous solutions, suspensions and emulsions for injection, freeze-dried agents, and suppositories. For injections, non-aqueous solutions and suspensions made from propylene glycol, polyethylene glycol, vegetable oils, such as olive oil, and esters such as ethyl oleate may be used. The basic materials of suppositories include Witepsol, macrogol, Tween 61, cacao butter, laurin, glycerol, and glycerogelatin.

Through the administration routes mentioned above, the α-galactosylceramide derivative of Chemical Formula 1 according to the present invention may be administered, either alone or in combination with an antigen or other immune adjuvant. In the latter case, the α-galactosylceramide derivative of Chemical Formula 1 may be administered along with dendritic cells or B cells loaded therewith.

In accordance with still another aspect thereof, the present invention provides a vaccine for oral or mucosal administration, comprising the pharmaceutical composition for use as an immune adjuvant of the present invention.

The α-galactosylceramide derivative of Chemical Formula 1 in accordance with the present invention may be administered at a dose that is effective in controlling immune responses. For example, the α-galactosylceramide derivative of Chemical Formula 1 may be administered to humans in a single dose or in multiple doses per day, each dose ranging from 1 to 250 μg/day, and preferably from 2 to 50 μg/day.

MODE FOR INVENTION

A better understanding of the present invention may be obtained through the following examples, which are set forth to illustrate, but are not to be construed as the limit of the present invention.

Example 1

α-Galactosylceramide Derivative 1

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-hexyl-1H-1,2,3-triazole The compound of Chemical Formula 2 (1.0 eq) and 1-octyne (1.5 eq) were mixed in a mixed solvent of t-butylalcohol/water (1:1, 0.2~0.5 M) to which 0.5 M copper (II) sulfide (10 mol % of 1-octyne %) and 1 M sodium ascorbate (40 mol % of 1-octyne) were then added at room temperature. After being stirred overnight at 50° C., the reaction mixture was diluted with ethylacetate and washed with brine. The ethylacetate layer was dried over magnesium sulfate, concentrated and purified through silica gel column chromatography (eluent=hexane/ethylacetate, 5:1 or 6:1) to afford the object compound as a colorless oil (120 mg, 77%-Intermediate 19).

$[\alpha]^{24}_D$ +20.5 (c 1.1, $CHCl_3$);

$^1$H NMR (300 MHz, $CDCl_3$) δ 0.85 (t, J=7.2 Hz, 3H), 0.88 (t, J=6.6 Hz, 3H), 1.26-1.57 (m, 40H), 2.56-2.63 (m, 2H), 3.16 (m, 1H), 3.44 (m, 2H), 3.68 (t, J=6.3 Hz, 1H), 3.76 (s, 3H), 3.74 (dd, J=3.0, 9.9 Hz, 1H), 3.79 (s, 3H), 3.89 (d, J=2.1 Hz, 1H), 3.99 (dd, J=3.9, 9.9 Hz, 1H), 4.05 (dd, J=3.9, 5.7 Hz, 1H), 4.19 (m, 2H), 4.31 (d, J=11.1 Hz, 2H), 4.33 (d, J=11.7 Hz, 1H), 4.44 (d, J=12.0 Hz, 2H), 4.47 (d, J=10.8 Hz, 1H), 4.52 (d, J=11.1 Hz, 1H), 4.55 (d, J=12.0 Hz, 1H), 4.67 (d, J=12.0 Hz, 1H), 4.68 (d, J=12.0 Hz, 1H), 4.74 (d, J=12.0 Hz, 1H), 4.81 (d, J=3.6 Hz, 1H), 4.88 (d, J=11.1 Hz, 1H), 4.94 (m, 1H), 6.81-6.86 (m, 4H), 7.12-7.36 (m, 24 H), 7.46 (s, 1H);

$^{13}$C NMR (75 MHz, $CDCl_3$) δ 14.0, 14.1, 22.5, 22.6, 25.4, 25.5, 29.0, 29.3, 29.4, 29.6, 29.7, 31.6, 31.9, 55.16, 55.19, 61.9, 67.3, 68.8, 69.7, 71.4, 72.8, 73.0, 73.4, 74.66, 74.69, 76.2, 78.2, 78.9, 79.1, 98.8, 113.7, 113.8, 121.7, 127.3, 127.4, 127.47, 127.52, 127.57, 127.63, 127.8, 128.1, 128.16, 128.23, 128.29, 128.32, 129.49, 129.53, 129.9, 130.3, 137.9, 138.4, 138.5, 138.6, 147.7, 159.1, 159.3;

HRMS (FAB) for $C_{76}H_{102}O_{10}N_3$ Calculated: 1216.7565 ([M+H]$^+$), Found: 1216.7572.

Step 2. Preparation of (2S,3R,4S,5R)-2-((2S,3S,4R)-2-(4-hexyl-1H-1,2,3-triazol-1-yl)-3,4-dihydroxyoctadecyloxy)-6-(hydroxymethyl)-tetrahydro-2H-pyrane-3,4,5-triol The compound (1.0 eq.) obtained in Step 1 was dissolved in a mixed solvent of ethylalcohol/methylene chloride (3:1, 0.01~0.1 M) to which Pd(OH)$_2$ (500 massa) was then added. The resulting reaction mixture was stirred for 5~8 hrs at room temperature under 1 atm of hydrogen gas. After the filtration of the metal catalyst through a Celite pad, the reaction mixture was washed with a solution of ethylalcohol/methylene chloride (3:1). After two rounds of centrifugation at 1000 rpm for 10 min, the supernatant was concentrated and dried in a vacuum. The concentrate was precipitated in a mixed solvent of hexane/ethyl acetate (1:1) to afford the object compound as a white wax solid (24 mg, 80%).

$^1$H NMR (300 MHz, $C_5D_5N$) δ 0.77 (t, J=6.6 Hz, 3H), 0.85 (t, J=6.9 Hz, 3H), 1.12-1.31 (m, 26H), 1.59-1.69 (m, 4H), 1.74-1.85 (m, 2H), 2.10-2.19 (m, 2H), 2.73 (t, J=7.5 Hz, 2H), 4.15 (m, 1H), 4.34-4.53 (m, 6H), 4.64 (dd, J=3.9, 9.9 Hz, 1H), 4.72 (dd, J=6.6, 11.4 Hz, 1H), 4.97 (dd, J=4.5, 11.4 Hz, 1H), 5.51 (d, J=3.6 Hz, 1H), 6.00 (td, J=3.9, 6.9 Hz, 1H), 8.27 (s, 1H);

$^{13}$C NMR (75 MHz, $C_5D_5N$) δ 14.2, 14.3, 22.8, 22.9, 26.2, 26.3, 29.2, 29.6, 29.86, 29.90, 30.0, 30.1, 30.2, 31.8, 32.1, 34.4, 62.7, 62.9, 67.4, 70.3, 71.0, 71.6, 72.2, 73.3, 76.8, 101.8, 122.1, 147.9;

HRMS (FAB) for $C_{32}H_{62}O_8N_3$ Calculated: 616.4537 ([M+H]$^+$), Found: 616.4540.

Example 2

Preparation of α-Galactosylceramide Derivative 2

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-heptyl-1H-1,2,3-triazole The same procedure as in Step 1 of Example 1 was conducted, with the exception that 1-nonyne was used instead of 1-octyne, to afford the object compound as colorless oil (83 mg, 75%).

$[\alpha]^{24}_D$ +20.4 (c 1.1, CHCl$_3$);

$^1$H NMR (300 MHz, CDCl$_3$) δ 0.87 (t, J=6.9 Hz, 3H), 0.89 (t, J=6.9 Hz, 3H), 1.27-1.61 (m, 42H), 2.57-2.63 (m, 2H), 3.08 (m, 1H), 3.47 (m, 2H), 3.71 (t, J=6.6 Hz, 1H), 3.77 (s, 3H), 3.79 (s, 3H), 3.81 (m, 1H), 3.91 (m, 1H), 4.00 (dd, J=3.6, 9.9 Hz, 1H), 4.11 (dd, J=3.6, 6.3 Hz, 1H), 4.18 (m, 2H), 4.28 (d, J=11.1 Hz, 1H), 4.35 (d, J=12.0 Hz, 1H), 4.37 (d, J=11.1 Hz, 1H), 4.45 (d, J=11.1 Hz, 2H), 4.51 (d, J=11.7 Hz, 1H), 4.54 (d, J=11.7 Hz, 1H), 4.59 (d, J=10.8 Hz, 1H), 4.65 (d, J=11.7 Hz, 1H), 4.69 (d, J=11.1 Hz, 1H), 4.77 (d, J=12.0 Hz, 1H), 4.83 (d, J=3.6 Hz, 1H), 4.89 (m, 1H), 4.90 (d, J=11.4 Hz, 1H), 6.82-6.86 (m, 4H), 7.16-7.37 (m, 24 H), 7.40 (s, 1H);

$^{13}$C NMR (75 MHz, CDCl$_3$) δ 14.0, 14.1, 22.6, 22.7, 25.4, 25.5, 29.1, 29.31, 29.34, 29.5, 29.6, 29.7, 31.7, 31.9, 55.19, 55.22, 62.0, 67.3, 68.8, 69.7, 71.5, 72.8, 73.0, 73.37, 73.42, 74.7, 76.2, 78.3, 78.9, 79.1, 98.8, 113.7, 113.8, 121.8, 127.3, 127.46, 127.49, 127.54, 127.6, 127.7, 127.8, 128.15, 128.18, 128.25, 128.31, 128.34, 129.5, 129.6, 129.9, 130.3, 137.9, 138.4, 138.5, 138.6, 147.6, 159.1, 159.3;

HRMS (FAB) for C$_{77}$H$_{104}$O$_{10}$N$_3$ Calculated: 1230.7722 ([M+H]$^+$), Found: 1230.7732.

Step 2. Preparation of (2S,3R,4S,5R)-2-((2S,3S,4R)-2-(4-heptyl-1H-1,2,3-triazol-1-yl)-3,4-dihydroxyoctadecyloxy)-6-(hydroxymethyl)-tetrahydro-2H-pyrane-3,4,5-triol The compound of Step 1 was used in a manner similar to that of Step 2 of Example 1 to afford the object compound as a white wax solid (38 mg, 75%).

$[\alpha]^{25}_D$ +20.4 (c 1.2, pyridine);

$^1$H NMR (300 MHz, C$_5$D$_5$N) δ 0.80 (t, J=6.9 Hz, 3H), 0.85 (t, J=6.9 Hz, 3H), 1.14-1.38 (m, 28H), 1.60-1.70 (m, 4H), 1.74-1.85 (m, 2H), 2.10-2.19 (m, 2H), 2.74 (t, J=7.8 Hz, 2H), 4.15 (br t, J=6.6 Hz, 1H), 4.34-4.53 (m, 6H), 4.64 (dd, J=3.9, 9.9 Hz, 1H), 4.72 (dd, J=6.6, 11.7 Hz, 1H), 4.97 (dd, J=4.2, 11.4 Hz, 1H), 5.51 (d, J=3.9 Hz, 1H), 6.00 (td, J=3.9, 6.9 Hz, 1H), 8.28 (s, 1H);

$^{13}$C NMR (75 MHz, C$_5$D$_5$N) δ 14.2, 14.3, 22.85, 22.92, 26.2, 26.3, 29.3, 29.5, 29.6, 29.9, 30.0, 30.1, 30.2, 31.9, 32.1, 34.4, 62.7, 62.9, 67.4, 70.3, 71.0, 71.6, 72.2, 73.3, 76.8, 101.8, 122.1, 147.9;

HRMS (FAB) for C$_{33}$H$_{64}$O$_8$N$_3$ Calculated: 630.4693 ([M+H]$^+$), Found: 630.4709.

Example 3

Preparation of α-Galactosylceramide Derivative 3

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-hexadecyl-1H-1,2,3-triazole The same procedure as in Step 1 of Example 1 was conducted except that 1-octadecyne was used as 1-alkyne, to afford the object compound as colorless oil (117 mg, 69%).

$[\alpha]^{24}_D$ +20.0 (c 1.2, CHCl$_3$);

$^1$H NMR (300 MHz, CDCl$_3$) δ 0.89 (t, J=6.9 Hz, 6H), 1.24-1.60 (m, 60H), 2.56-2.63 (m, 2H), 1.08 (m, 1H), 3.46 (m, 2H), 3.70 (t, J=6.6 Hz, 1H), 3.77 (s, 3H), 3.79 (s, 3H), 3.80 (dd, J=2.7, 10.2 Hz, 1H), 3.90 (d, J=2.1 Hz, 1H), 4.00 (dd, J=3.6, 10.2 Hz, 1H), 4.10 (dd, J=3.3, 6.3 Hz, 1H), 4.20 (m, 2H), 4.28 (d, J=11.1 Hz, 1H), 4.35 (d, J=11.1 Hz, 1H), 4.36 (d, J=11.1 Hz, 1H), 4.45 (d, J=11.7 Hz, 2H), 4.51 (d, J=11.7 Hz, 1H), 4.54 (d, J=11.7 Hz, 1H), 4.58 (d, J=10.5 Hz, 1H), 4.66 (d, K=12.0 Hz, 1H), 4.69 (d, J=11.7 Hz, 1H), 4.76 (d, J=11.7 Hz, 1H), 4.83 (d, J=3.6 Hz, 1H), 4.896 (m, 1H), 4.898 (d, J=11.7 Hz, 1H), 6.81-6.86 (m, 4H), 7.15-7.37 (m, 24H), 7.41 (s, 1H);

$^{13}$C NMR (75 MHz, CDCl$_3$) δ 14.1, 22.6, 25.4, 25.6, 29.3, 29.38, 29.44, 29.5, 29.6, 29.7, 31.9, 55.1, 55.2, 61.9, 67.3, 68.8, 69.7, 71.4, 72.8, 72.9, 73.4, 73.7, 76.2, 78.2, 78.9, 79.0, 98.8, 113.6, 113.8, 121.7, 127.3, 127.4, 127.46, 127.51, 127.6, 127.7, 128.1, 128.15, 128.22, 128.29, 128.31, 129.49, 129.54, 129.9, 130.3, 137.9, 138.4, 138.5, 138.6, 147.8, 159.1, 159.3;

HRMS (FAB) for C$_{86}$H$_{122}$O$_{10}$N$_3$ Calculated: 1356.9130 ([M+H]$^+$), Found: 1356.9163.

Step 2. Preparation of (2S,3R,4S,5R)-2-((2S,3S,4R)-2-(4-hexadecyl-1H-1,2,3-triazol-1-yl)-3,4-dihydroxyoctadecyloxy)-6-(hydroxymethyl)-tetrahydro-2H-pyrane-3,4,5-triol The compound of Step 1 was used in a manner similar to that of Step 2 of Example 1, to afford the object compound as a white solid (24 mg, 73%).

m.p. 162-164° C.;

$[\alpha]^{25}_D$ +39.0 (c 0.5, pyridine);

$^1$H NMR (300 MHz, C$_5$D$_5$N) δ 0.85 (t, J=6.9 Hz, 6H), 1.23-1.31 (m, 46H), 1.59-1.85 (m, 6H), 2.10-2.19 (m, 2H), 2.77 (t, J=7.8 Hz, 2H), 4.15 (br t, J=7.2 Hz, 1H), 4.34-4.53 (m, 6H), 4.64 (dd, J=3.9, 9.9 Hz, 1H), 4.72 (dd, J=6.6, 11.4 Hz, 1H), 4.98 (dd, J=4.5, 11.4 Hz, 1H), 5.51 (d, J=3.9 Hz, 1H), 6.00 (td, J=3.9, 7.2 Hz, 1H), 8.29 (s, 1H);

$^{13}$C NMR (75 MHz, C$_5$D$_5$N) δ 14.3, 22.9, 26.3, 29.6, 29.7, 29.9, 30.0, 30.1, 30.2, 32.1, 34.4, 62.7, 62.9, 67.4, 70.3, 71.0, 71.6, 72.2, 73.3, 76.8, 101.8, 122.1, 147.9;

HRMS (FAB) for C$_{42}$H$_{82}$O$_8$N$_3$ Calculated: 757.6102 ([M+H]$^+$), Found: 756.6105.

Example 4

Preparation of α-Galactosylceramide Derivative 4

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-tricosyl-1H-1,2,3-triazole The same procedure of Step 1 of Example 1 was conducted except that 1-pentacosyne was used as the 1-alkyne, to afford the object compound as a colorless oil (94 mg, 72%).

$[\alpha]^{24}_D$ +18.1 (c 1.1, CHCl$_3$);

$^1$H NMR (300 MHz, CDCl$_3$) δ 0.89 (t, J=6.9 Hz, 6H), 1.27-1.57 (m, 74H), 2.60 (m, 2H), 3.09 (m, 1H), 3.46 (m, 2H), 3.70 (t, J=6.3 Hz, 1H), 3.76 (s, 3H), 3.79 (s, 3H), 3.80 (dd, J=2.4, 9.9 Hz, 1H), 3.90 (m, 1H), 4.00 (dd, J=3.9, 9.9 Hz, 1H), 4.10 (dd, J=3.6, 6.0 Hz, 1H), 4.18 (m, 2H), 4.28 (d, J=11.1 Hz, 1H), 4.35 (d, J=11.7 Hz, 1H), 4.36 (d, J=10.8 Hz, 1H), 4.45 (d, J=11.7 Hz, 2H), 4.51 (d, J=11.7 Hz, 1H), 4.54 (d, J=11.7 Hz, 1H), 4.58 (d, J=10.8 Hz, 1H), 4.66 (d, J=11.7 Hz, 1H), 4.69 (d, J=11.4 Hz, 1H), 4.76 (d, J=11.7 Hz, 1H), 4.83 (d, J=3.6 Hz, 1H), 4.895 (m, 1H), 4.896 (d, J=11.4 Hz, 1H), 6.81-6.85 (m, 4H), 7.15-7.37 (m, 24 H), 7.41 (s, 1H);

$^{13}$C NMR (75 MHz, CDCl$_3$) δ 14.1, 22.7, 25.4, 25.5, 29.3, 29.4, 29.5, 29.7, 31.9, 55.17, 55.21, 62.0, 67.3, 68.8, 69.7, 71.5, 72.8, 73.0, 73.37, 73.41, 74.7, 76.2, 78.3, 78.9, 79.1, 98.8, 113.7, 113.8, 121.8, 127.3, 127.46, 127.48, 127.53, 127.6, 127.8, 128.1, 128.17, 128.24, 128.30, 128.33, 129.5, 129.6, 129.9, 130.3, 137.9, 138.4, 138.5, 138.6, 147.6, 159.1, 159.3;

HRMS (FAB) for $C_{93}H_{136}O_{10}N_3$ Calculated: 1455.0226 ([M+H]$^+$), Found: 1455.0216.

Step 2. Preparation of (2S,3R,4S,5R)-2-((2S,3S,4R)-3,4-dihydroxy-2-(4-tricosyl-1H-1,2,3-triazol-1-yl) octadecyloxy)-6-(hydroxymethyl)-tetranydro-2H-pyrane-3,4,5-triol The compound of Step 1 was used in a manner similar to that of Step 2 of Example 1, to afford the object compound as a white solid ((18 mg, 75%).
m.p. 163-165° C.;
[α]$^{25}_D$, +42.8 (c 0.4, pyridine);
$^1$H NMR (300 MHz, $C_5D_5N$) δ 0.86 (t, J=6.9 Hz, 6H), 1.23-1.40 (m, 60H), 1.59-1.85 (m, 6H), 2.10-2.19 (m, 2H), 2.77 (t, J=7.5 Hz, 2H), 4.15 (m, 1H), 4.31-4.53 (m, 6H), 4.64 (dd, J=3.9, 9.9 Hz, 1H), 4.72 (dd, J=6.9, 11.4 Hz, 1H), 4.98 (dd, J=4.5, 11.4 Hz, 1H), 5.51 (d, J=3.6 Hz, 1H), 6.00 (td, J=3.9, 6.9 Hz, 1H), 8.29 (s, 1H);
$^{13}$C NMR (75 MHz, $C_5D_5N$) δ 14.3, 22.9, 26.3, 29.6, 29.7, 29.9, 30.0, 30.2, 32.1, 34.4, 62.7, 62.9, 67.4, 70.3, 71.0, 71.6, 72.2, 73.3, 76.8, 101.8, 122.1, 147.9;
HRMS (FAB) for $C_{49}H_{96}O_8N_3$ Calculated: 854.7197 ([M+]$^+$), Found: 854.7212.

Example 5

Preparation of α-Galactosylceramide 5

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-tetracosyl-1H-1,2,3-triazole The same procedure of Step 1 of Example 1 was conducted except that 1-hexacosyne was used as the 1-alkyne, to afford the object compound as a colorless oil (187 mg, 72%).
[α]$^{24}_D$ +17.9 (c 1.2, $CHCl_3$);
$^1$H NMR (300 MHz, $CDCl_3$) δ 0.89 (t, J=6.9 Hz, 6H), 1.27-1.57 (m, 76H), 2.60 (m, 2H), 3.11 (m, 1H), 3.46 (m, 2H), 3.70 (t, J=6.3 Hz, 1H), 3.77 (s, 3H), 3.79 (s, 3H), 3.80 (m, 1H), 3.90 (d, J=1.8 Hz, 1H), 3.99 (dd, J=3.6, 9.9 Hz, 1H), 4.09 (dd, J=3.6, 6.3 Hz, 1H), 4.18 (m, 2H), 4.29 (d, J=11.4 Hz, 1H), 4.35 (d, J=11.4 Hz, 2H), 4.45 (d, J=11.7 Hz, 2H), 4.51 (d, J=11.7 Hz, 1H), 4.53 (d, J=11.7 Hz, 1H), 4.57 (d, J=11.7 Hz, 1H), 4.66 (d, J=12.0 Hz, 1H), 4.69 (d, J=11.4 Hz, 1H), 4.76 (d, J=11.7 Hz, 1H), 4.82 (d, J=3.6 Hz, 1H), 4.89 (d, J=11.4 Hz, 1H), 4.90 (m, 1H), 6.82-6.86 (m, 4H), 7.15-7.37 (m, 24 H), 7.42 (s, 1H);
$^{13}$C NMR (75 MHz, $CDCl_3$) δ 14.1, 22.6, 25.4, 25.6, 29.30, 29.31, 29.36, 29.43, 29.5, 29.59, 29.64, 29.7, 31.9, 55.11, 55.14, 61.8, 67.3, 68.8, 69.6, 71.4, 72.7, 72.9, 73.4, 74.7, 76.2, 78.2, 78.8, 79.0, 98.7, 113.6, 113.7, 121.6, 127.3, 127.4, 127.49, 127.54, 127.6, 127.7, 128.11, 128.13, 128.2, 128.26, 128.29, 129.48, 129.52, 129.9, 130.2, 137.9, 138.4, 138.5, 138.6, 147.8, 159.1, 159.2;
HRMS (FAB) for $C_{94}H_{137}O_{10}N_3$ Calculated: 1468.0304 (M+), Found: 1468.0286.

Step 2. Preparation of (2S,3R,4S,5R)-2-((2S,3S,4R)-3,4-dihydroxy-2-(4-tetracosyl-1H-1,2,3-triazol-1-yl) octadecyloxy)-6-(hydroxymethyl)-tetrahydro-2H-pyrane-3,4,5-triol The compound of Step 1 was used in a manner similar to that of Step 2 of Example 1, to afford the object compound as a white solid (31 mg, 77%).
m.p. 167-169° C.;
[α]$^{25}_D$ +41.9 (c 1.5, pyridine);
$^1$H NMR (300 MHz, $C_5D_5N$) δ 0.86 (t, J=6.9 Hz, 6H), 1.24-1.38 (m, 62H), 1.56-1.83 (m, 6H), 2.10-2.21 (m, 2H), 2.76 (t, J=7.5 Hz, 2H), 4.13 (m, 1H), 4.32-4.51 (m, 6H), 4.61 (dd, J=3.9, 9.9 Hz, 1H), 4.69 (dd, J=6.9, 11.1 Hz, 1H), 4.95 (dd, J=4.5, 10.8 Hz, 1H), 5.48 (d, J=3.6 Hz, 1H), 5.98 (td, J=3.9, 6.9 Hz, 1H), 8.27 (s, 1H);
$^{13}$C NMR (75 MHz, $C_5D_5N$) δ 14.3, 22.9, 26.25, 26.29, 29.61, 29.64, 29.8, 29.9, 30.0, 30.2, 32.1, 34.3, 62.7, 62.8, 67.4, 70.2, 71.0, 71.5, 72.2, 73.2, 76.7, 101.7, 122.1, 147.9;
HRMS (FAB) for $C_{50}H_{98}O_8N_3$ Calculated: 868.7354 ([M+H]$^+$), Found: 868.7361.

Example 6

Preparation of α-Galactosylceramide 6

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-pentacosyl-1H-1,2,3-triazole The same procedure as in Step 1 of Example 1 was conducted, except that 1-heptacosyne was used as the 1-alkyne, to afford the object compound as colorless oil (98 mg, 73%).
[α]$^{24}_D$ +18.8 (c 1.0, $CHCl_3$);
$^1$H NMR (300 MHz, $CDCl_3$) δ 0.89 (t, J=6.9 Hz, 6H), 1.28-1.59 (m, 78H), 2.61 (m, 2H), 3.09 (m, 1H), 3.48 (m, 2H), 3.72 (t, J=6.3 Hz, 1H), 3.77 (s, 3H), 3.79 (s, 3H), 3.81 (m, 1H), 3.90 (m, 1H), 4.01 (dd, J=3.3, 10.2 Hz, 1H), 4.11 (dd, J=3.3, 6.6 Hz, 1H), 4.19 (m, 2H), 4.28 (d, J=11.1 Hz, 1H), 4.36 (d, J=12.0 Hz, 1H), 4.38 (d, J=11.4 Hz, 1H), 4.46 (d, J=11.4 Hz, 2H), 4.52 (d, J=11.7 Hz, 1H), 4.55 (d, J=11.7 Hz, 1H), 4.60 (d, J=11.1 Hz, 1H), 4.67 (d, J=11.7 Hz, 1H), 4.71 (d, J=11.7 Hz, 1H), 4.78 (d, J=11.7 Hz, 1H), 4.84 (d, J=3.9 Hz, 1H), 4.89 (m, 1H), 4.91 (d, J=11.4 Hz, 1H), 6.82-6.86 (m, 4H), 7.16-7.38 (m, 24 H), 7.41 (s, 1H);
$^{13}$C NMR (75 MHz, $CDCl_3$) d14.1, 22.7, 25.4, 25.6, 29.32, 29.33, 29.4, 29.45, 29.52, 29.66, 29.69, 31.9, 55.15, 55.18, 61.9, 67.3, 68.8, 69.7, 71.5, 72.8, 72.9, 73.4, 74.7, 76.2, 78.3, 78.8, 79.1, 98.8, 113.7, 113.8, 121.7, 127.2, 127.3, 127.4, 127.46, 127.51, 127.56, 127.62, 127.7, 128.1, 128.15, 128.23, 128.29, 128.32, 129.49, 129.54, 129.9, 130.3, 137.9, 138.4, 138.5, 138.6, 147.8, 159.1, 159.3;
HRMS (FAB) for $C_{95}H_{140}O_{10}N_3$ Calculated: 1483.0539 ([M+H]$^+$), Found: 1483.0570.

Step 2. Preparation of (2S,3R,4S,5R)-2-((2S,3S,4R)-3,4-dihydroxy-2-(4-pentacosyl-1H-1,2,3-triazol-1-yl)octadecyloxy)-6-(hydroxymethyl)-tetrahydro-2H-pyrane-3,4,5-triol The compound of Step 1 was used in a manner similar to that of Step 2 of Example 1, to afford the object compound as a white solid (17 mg, 70%).
m.p. 165-167° C.;
[α]$^{25}_D$ +35.8 (c 0.6, pyridine);
$^1$H NMR (300 MHz, $C_5D_5N$) δ 0.86 (t, J=6.6 Hz, 6H), 1.24-1.34 (m, 64H), 1.59-1.85 (m, 6H), 2.10-2.19 (m, 2H), 2.77 (t, J=7.5 Hz, 2H), 4.15 (br t, J=6.9 Hz, 1H), 4.34-4.53 (m, 6H), 4.64 (dd, J=3.9, 9.9 Hz, 1H), 4.71 (dd, J=6.6, 11.4 Hz, 1H), 4.98 (dd, J=4.2, 11.4 Hz, 1H), 5.50 (d, J=3.6 Hz, 1H), 6.00 (td, J=3.9, 6.9 Hz, 1H), 8.29 (s, 1H);

$^{13}$C NMR (75 MHz, C$_5$D$_5$N) δ 14.3, 22.9, 26.3, 29.6, 29.7, 29.8, 29.9, 30.0, 30.2, 32.1, 34.4, 62.7, 62.9, 67.4, 70.3, 71.0, 71.6, 72.2, 73.3, 76.8, 101.8, 122.1, 147.9;

HRMS (FAB) for C$_{51}$H$_{100}$O$_8$N$_3$ Calculated: 882.7510 ([M+H]$^+$), Found: 882.7508.

Example 7

Preparation of α-Galactosylceramide Derivative 7

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(6-phenylhexyl)-1H-1,2,3-triazole The same procedure as in Step 1 of Example 1 was conducted, except that oct-7-ynyl-benzene was used as the 1-alkyne, followed by silica gel column chromatography eluting with a mixture of 4:1 or 3:1 hexane/ethylacetate to obtain the object compound as a white wax (230 mg, 88%).

$^1$H NMR (300 MHz, CDCl$_3$) δ 0.89 (t, J=6.6 Hz, 3H), 1.26-1.63 (m, 34H), 2.54-2.62 (m, 4H), 3.08 (m, 1H), 3.46 (m, 2H), 3.70 (t, J=6.6 Hz, 1H), 3.76 (s, 3H), 3.78 (s, 3H), 3.81 (dd, J=2.7, 8.7 Hz, 1H), 3.89 (d, J=1.2 Hz, 1H), 3.99 (dd, J=3.9, 9.9 Hz, 1H), 4.09 (dd, J=3.3, 6.6 Hz, 1H), 4.17-4.29 (m, 3H), 4.33 (d, J=6.0 Hz, 1H), 4.37 (d, J=5.1 Hz, 1H), 4.44 (d, J=11.7 Hz, 2H), 4.50 (d, J=7.2 Hz, 1H), 4.53 (d, J=6.6 Hz, 1H), 4.57 (d, J=10.5 Hz, 1H), 4.65 (d, J=11.7 Hz, 1H), 4.68 (d, J=11.7 Hz, 1H), 4.75 (d, J=11.7 Hz, 1H), 4.83 (d, J=3.3 Hz, 1H), 4.89 (d, J=11.7 Hz, 2H), 6.80-6.86 (m, 4H), 7.13-7.36 (m, 29H), 7.39 (s, 1H).

Step 2. Preparation of (2S,3R,4S,5R)-2-((2S,3S,4R)-3,4-dihydroxy-2-(4-(6-phenylhexyl)-1H-1,2,3-triazol-1-yl)octadecyloxy)-6-(hydroxymethyl)-tetrahydro-2H-pyrane-3,4,5-triol The compound of Step 1 was used in a manner similar to that of Step 2 of Example 1, to afford the object compound as a white wax (20 mg, 80%).

$^1$H NMR (300 MHz, pyridine) δ 0.84 (t, J=6.8 Hz, 3H), 1.13-1.44 (m, 24H), 1.49-1.89 (m, 8H), 2.04-2.24 (m, 2H), 2.54 (t, J=7.5 Hz, 2H), 2.73 (m, 2H), 4.16 (m, 1H), 4.35-4.78 (m, 7H), 5.52 (d, J=3.8 Hz, 1H), 6.02 (m, 1H), 7.20-7.37 (m, 6H).

Example 8

Preparation of α-Galactosylceramide 8

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(7-phenylheptyl)-1H-1,2,3-triazole The same procedure as in Step 1 of Example 1 was conducted, except that non-8-ynyl-benzene was used as the 1-alkyne, followed by silica gel column chromatography eluting with a mixture of 4:1 or 3:1 hexane/ethylacetate to obtain the object compound as a white wax (130 mg, 85%).

$^1$H NMR (300 MHz, CDCl$_3$) δ 0.89 (t, J=6.6 Hz, 3H), 1.13-1.58 (m, 36H), 2.54-2.62 (m, 4H), 3.08 (m, 1H), 3.46 (m, 2H), 3.71 (t, J=6.6 Hz, 1H), 3.76 (s, 3H), 3.78 (s, 3H), 3.81 (dd, J=2.7, 8.7 Hz, 1H), 3.91 (d, J=2.4 Hz, 1H), 3.98 (dd, J=3.6, 9.9 Hz, 1H), 4.09 (dd, J=3.3, 6.6 Hz, 1H), 4.17-4.29 (m, 3H), 4.33 (d, J=6.0 Hz, 1H), 4.37 (d, J=5.1 Hz, 1H), 4.44 (d, J=11.7 Hz, 2H), 4.50 (d, J=7.2 Hz, 1H), 4.54 (d, J=6.6 Hz, 1H), 4.58 (d, J=10.8 Hz, 1H), 4.65 (d, J=11.7 Hz, 1H), 4.69 (d, J=11.7 Hz, 1H), 4.75 (d, J=11.7 Hz, 1H), 4.83 (d, J=3.6 Hz, 1H), 4.90 (d, J=11.7 Hz, 2H), 6.81-6.86 (m, 4H), 7.14-7.37 (m, 29H), 7.40 (s, 1H).

Step 2. Preparation of (2S,3R,4S,5R)-2-((2S,3S,4R)-3,4-dihydroxy-2-(4-(7-phenylheptyl)-1H-1,2,3-triazol-1-yl)octadecyloxy)-6-(hydroxymethyl)-tetrahydro-2H-pyrane-3,4,5-triol The compound of Step 1 was used in a manner similar to that of Step 2 of Example 1, to afford the object compound as a white wax solid (15 mg, 72%).

$^1$H NMR (300 MHz, pyridine) δ 0.85 (t, J=6.8 Hz, 3H), 1.11-1.42 (m, 26H), 1.49-1.89 (m, 8H), 2.03-2.25 (m, 2H), 2.54 (t, J=7.5 Hz, 2H), 2.72 (m, 2H), 4.14 (m, 1H), 4.35-4.77 (m, 7H), 5.52 (d, J=3.9 Hz, 1H), 6.02 (m, 1H), 7.21-7.37 (m, 6H).

Example 9

Preparation of α-Galactosylceramide 9

Step 1. Preparation of 1-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-4-(8-phenyloctyl)-1H-1,2,3-triazole The same procedure as in Step 1 of Example 1 was conducted except that non-8-ynyl-benzene was used as the 1-alkyne, followed by silica gel column chromatography eluting with a mixture of 4:1 or 3:1 hexane/ethylacetate to obtain the object compound as a white wax (80 mg, 82%).

$^1$H NMR (300 MHz, CDCl$_3$) δ 0.91 (t, J=6.7 Hz, 3H), 1.15-1.60 (m, 38H), 2.58-2.64 (m, 4H), 3.10 (m, 1H), 3.49 (m, 2H), 3.73 (t, J=6.6 Hz, 1H), 3.78 (s, 3H), 3.81 (s, 3H), 3.84 (dd, J=2.7, 8.6 Hz, 1H), 3.92 (d, J=1.8 Hz, 1H), 4.02 (dd, J=3.9, 9.9 Hz, 1H), 4.12 (dd, J=3.3, 6.6 Hz, 1H), 4.19-4.31 (m, 3H), 4.35 (d, J=6.0 Hz, 1H), 4.38 (d, J=5.1 Hz, 1H), 4.46 (d, J=11.7 Hz, 2H), 4.52 (d, J=7.2 Hz, 1H), 4.55 (d, J=6.6 Hz, 1H), 4.58 (d, J=10.5 Hz, 1H), 4.68 (d, J=11.7 Hz, 1H), 4.70 (d, J=11.7 Hz, 1H), 4.77 (d, J=11.7 Hz, 1H), 4.84 (d, J=3.3 Hz, 1H), 4.91 (d, J=11.7 Hz, 2H), 6.83-6.88 (m, 4H), 7.17-7.39 (m, 29H), 7.42 (s, 1H).

Step 2. Preparation of (2S,3R,4S,5R)-2-((2S,3S,4R)-3,4-dihydroxy-2-(4-(8-phenyloctyl)-1H-1,2,3-triazol-1-yl)octadecyloxy)-6-(hydroxymethyl)-tetrahydro-2H-pyrane-3,4,5-triol The compound of Step 1 was used in a manner similar to that of Step 2 of Example 1, to afford the object compound as a white solid (18 mg, 73%).

$^1$H NMR (300 MHz, pyridine) δ 0.85 (t, J=6.8 Hz, 3H), 1.13-1.44 (m, 28H), 1.49-1.89 (m, 8H), 2.06-2.25 (m, 2H), 2.54 (t, J=7.5 Hz, 2H), 2.75 (m, 2H), 4.16 (m, 1H), 4.35-4.77 (m, 7H), 5.52 (d, J=3.9 Hz, 1H), 6.02 (m, 1H), 7.19-7.37 (m, 6H).

Example 10

Preparation of α-Galactosylceramide Derivative 10

Step 1. Preparation of benzyl (13S,14S,15R)-14,15-bis(4-methoxybenzyloxy)-11-oxo-13-(((2S,3R,4S,5S)-3,4,5-tris(benzyloxy)-6-(benzyloxymethyl)-tetrahydro-2H-pyran-2-yloxy)methyl) nonacosylcarbamate The compound of Chemical Formula 3 (1.0 eq) and 11-benzyloxycarbonyl amino-undecanoic acid (acid, 1.2 eq) were mixed in a dry methylene chloride (0.2~0.5 M) solution to which N-(3-dimethylaminopropyl)-N'-ethylcarbodiimide hydrochloride (1.5 eq) and 4-methylaminopyridine (0.1 eq) were then added at room temperature. After being stirred for 1~2 hrs at room temperature, the reaction mixture was diluted with ethylacetate and washed with brine. The ethylacetate layer was dried over magnesium sulfate, concentrated, and purified through silica gel column chromatography (eluent hexane/ethylacetate, 3:1 or 2:1) to afford the object compound as a colorless oil (157 mg, 81%).

$^1$H NMR (300 MHz, $CDCl_3$) δ 0.93 (t, J=6.6 Hz, 3H), 1.22-1.72 (m, 43H), 1.98 (m, 1H), 3.19 (m, 2H), 3.52 (m, 2H), 3.78 (m, 1H), 3.77 (s, 3H), 3.79 (s, 3H), 3.87 (dd, J=2.4, 6.9 Hz, 1H), 3.93-4.21 (m, 6H), 4.22 (m, 1H), 4.38 (d, J=4.8 Hz, 1H), 4.42 (d, J=5.7 Hz, 1H), 4.51 (d, J=10.8 Hz, 1H), 4.53 (d, J=12.0 Hz, 1H), 4.58 (d, J=4.2 Hz, 1H), 4.66 (d, J=13.2 Hz, 1H), 4.73 (d, J=9.9 Hz, 2H), 4.77 (d, J=13.5 Hz, 1H), 4.84 (d, J=11.7 Hz, 1H), 4.85 (d, J=12.0 Hz, 1H), 4.91 (d, J=3.6 Hz, 1H), 4.97 (d, J=11.4 Hz, 1H), 5.13 (s, 2H), 6.15 (d, J=8.7 Hz, 1H), 6.86 (t, J=8.1 Hz, 4H), 7.26-7.43 (m, 29H).

Step 2. Preparation of 11-amino-N-((2S,3S,4R)-3,4-dihydroxy-1-(((2S,3R,4S,5R)-3,4,5-trihydroxy-6-(hydroxymethyl)-tetrahydro-2H-pyran-2-yloxy)octadecan-2-yl)undecanamide The compound of Step 1 was used in a manner similar to that of Step 2 of Example 1, to afford the object compound as a white solid (45 mg, 80%).

$^1$H NMR (300 MHz, $C_5D_5N$) δ 0.84 (t, J=6.8 Hz, 3H), 1.08-1.43 (m, 36H), 1.62 (m, 1H), 1.75-2.01 (m, 5H), 2.23 (m, 1H), 2.58 (m, 2H), 3.25 (t, J=7.5 Hz, 1H), 4.30-4.65 (m, 10H), 5.26 (m, 1H), 5.53 (d, J=3.0 Hz, 1H), 9.16 (d, J=10.8 Hz, 1H).

Example 11

Preparation of α-Galactosylceramide 11

Step 1. Preparation of benzyl (14S,15S,16R)-15,16-bis(4-methoxybenzyloxy)-12-oxo-14-(((2S,3R,4S,5S)-3,4,5-tris(benzyloxy)-6-(benzyloxymethyl)-tetrahydro-2H-pyran-2-yloxy)methyl)triacontyl carbamate The same procedure as in Step 1 of Example 10 was conducted, except that 12-benzyloxycarbonylamino-dodecanoic acid was used as the acid, to afford the object compound as a colorless oil (149 mg, 76%).

$^1$H NMR (300 MHz, $CDCl_3$) δ 0.93 (t, J=6.6 Hz, 3H), 1.22-1.72 (m, 45H), 1.98 (m, 1H), 3.20 (m, 2H), 3.52 (m, 2H), 3.76 (m, 1H), 3.78 (s, 3H), 3.80 (s, 3H), 3.87 (dd, J=2.7, 6.9 Hz, 1H), 3.93-4.13 (m, 6H), 4.22 (m, 1H), 4.38 (d, J=5.7 Hz, 1H), 4.42 (d, J=6.6 Hz, 1H), 4.51 (d, J=11.1 Hz, 1H), 4.53 (d, J=11.7 Hz, 1H), 4.58 (d, J=4.2 Hz, 1H), 4.66 (d, J=13.8 Hz, 1H), 4.73 (d, J=11.1 Hz, 2H), 4.77 (d, J=11.4 Hz, 1H), 4.83 (d, J=11.4 Hz, 1H), 4.85 (d, J=12.0 Hz, 1H), 4.91 (d, J=3.6 Hz, 1H), 4.97 (d, J=11.7 Hz, 1H), 5.13 (s, 2H), 6.15 (d, J=8.7 Hz, 1H), 6.87 (t, J=8.4 Hz, 4H), 7.26-7.43 (m, 29H).

Step 2. Preparation of 12-amino-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)dodecanamide The compound of Step 1 was used in a manner similar to that of Step 2 of Example 1, to afford the object compound as a white solid (50 mg, 86%).

$^1$H NMR (300 MHz, $C_5D_5N$) δ 0.84 (t, J=6.8 Hz, 3H), 1.08-1.43 (m, 38H), 1.61 (m, 1H), 1.75-2.32 (m, 6H), 2.59 (m, 2H), 3.25 (t, J=7.5 Hz, 1H), 4.30-4.61 (m, 10H), 5.24 (m, 1H), 5.53 (d, J=3.4 Hz, 1H), 9.17 (d, J=8.7 Hz, 1H).

Example 12

Preparation of α-Galactosylceramide 12

Step 1. Preparation of (13S,14S,15R)-1-(benzyloxy)-14,15-bis(4-methoxybenzyloxy)-13-(((2S,3R,4S,5S)-3,4,5-tris(benzyloxy)-6-(benzyloxymethyl)-tetrahydro-2H-pyran-2-yloxy)methyl)nonacosan-11-one The same procedure as in Step 1 of Example 10 was conducted, except that 11-benzyloxy-undecanoic acid was used as the acid, to afford the object compound as a colorless oil (75 mg, 77%).

$^1$H NMR (300 MHz, $CDCl_3$) δ 0.88 (t, J=6.6 Hz, 3H), 1.22-1.96 (m, 44H), 3.40-3.53 (m, 4H), 3.71 (m, 1H), 3.75 (s, 3H), 3.77 (s, 3H), 3.81 (dd, J=2.4, 6.9 Hz, 1H), 3.87-4.07 (m, 6H), 4.15 (m, 1H), 4.33 (d, J=7.8 Hz, 1H), 4.37 (d, J=8.7 Hz, 1H), 4.43 (d, J=9.9 Hz, 2H), 4.50 (s, 2H), 4.51 (d, J=9.3 Hz, 1H), 4.56 (d, J=11.4 Hz, 1H), 4.65 (d, J=11.7 Hz, 1H), 4.68 (d, J=11.1 Hz, 1H), 4.72 (d, J=12.0 Hz, 1H), 4.80 (d, J=11.4 Hz, 1H), 4.81 (d, J=11.7 Hz, 1H), 4.85 (d, J=3.6 Hz, 1H), 4.92 (d, J=11.7 Hz, 1H), 6.10 (d, J=8.7 Hz, 1H), 6.82 (m, 4H), 7.21-7.38 (m, 29H).

Step 2. Preparation of N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-hydroxyundecanamide The compound of Step 1 was used in a manner similar to that of Step 2 of Example 1, to afford the object compound as a white wax solid (22 mg, 80%).

$^1$H NMR (300 MHz, $C_5D_5N$) δ 0.84 (t, J=6.8 Hz, 3H), 1.12-1.48 (m, 36H), 1.59-1.76 (m, 6H), 2.24 (m, 1H), 2.50 (t, J=7.5 Hz, 1H), 3.85 (t, J=6.3 Hz, 2H), 4.30-4.69 (m, 10H), 5.26 (m, 1H), 5.55 (d, J=3.9 Hz, 1H), 8.53 (d, J=8.7 Hz, 1H).

Example 13

Preparation of α-Galactosylceramide 13

Step 1. Preparation of (14S,15S,16R)-1-(benzyloxy)-15,16-bis(4-methoxybenzyloxy)-14-(((2S,3R,4S,5S)-3,4,5-tris(benzyloxy)-6-(benzyloxymethyl)-tetrahydro-2H-pyran-2-yloxy)methyl)triacontan-12-one The same procedure as in Step 1 of Example 10 was conducted, except that 12-benzyloxy-dodecanoic acid was used as the acid, to afford the object compound as a colorless oil (70 mg, 81%).

¹H NMR (300 MHz, CDCl₃) δ 0.88 (t, J=6.6 Hz, 3H), 1.21-1.96 (m, 46H), 3.39-3.59 (m, 4H), 3.71 (m, 1H), 3.74 (s, 3H), 3.77 (s, 3H), 3.80 (dd, J=2.4, 6.9 Hz, 1H), 3.87-4.07 (m, 6H), 4.15 (m, 1H), 4.33 (d, J=7.8 Hz, 1H), 4.37 (d, J=8.7 Hz, 1H), 4.43 (d, J=10.2 Hz, 2H), 4.50 (s, 2H), 4.51 (d, J=8.1 Hz, 1H), 4.56 (d, J=11.7 Hz, 1H), 4.65 (d, J=11.1 Hz, 1H), 4.68 (d, J=11.1 Hz, 1H), 4.75-4.82 (m, 3H), 4.85 (d, J=3.6 Hz, 1H), 4.92 (d, J=11.7 Hz, 1H), 6.09 (d, J=8.7 Hz, 1H), 6.82 (m, 4H), 7.20-7.38 (m, 29H).

Step 2. Preparation of N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-12-hydroxydodecanamide The compound of Step 1 was used in a manner similar to that of Step 2 of Example 1, to afford the object compound as a white wax solid (24 mg, 78%).

¹H NMR (300 MHz, C₅D₅N) δ 0.84 (t, J=6.8 Hz, 3H), 1.15-1.51 (m, 38H), 1.58-1.89 (m, 6H), 2.24 (m, 1H), 2.52 (t, J=7.5 Hz, 1H), 3.86 (t, J=6.3 Hz, 2H), 4.28-4.69 (m, 10H), 5.26 (m, 1H), 5.55 (d, J=3.9 Hz, 1H), 8.91 (d, J=8.1 Hz, 1H).

Example 14

Preparation of α-Galactosylceramide 16

Step 1. Preparation of N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-8-(diheptylamino)octanamide The same procedure as in Step 1 of Example 10 was conducted, except that 8-diheptylamino-octanoic acid was used as an acid, followed by silica gel column chromatography eluting with a mixture of 15:1 or 10:1 methylene chloride/methanol to obtain the object compound as a yellow oil (120 mg, 90%).

¹H NMR (300 MHz, CDCl₃) δ 0.88 (t, J=6.6 Hz, 9H), 1.22-2.04 (m, 60H), 2.91 (m, 4H), 3.40-3.53 (m, 3H), 3.67-3.82 (m, 2H), 3.75 (s, 3H), 3.77 (s, 3H), 3.89-4.07 (m, 4H), 4.16 (m, 1H), 4.33 (d, J=7.8 Hz, 1H), 4.37 (d, J=8.7 Hz, 1H), 4.43 (d, J=10.8 Hz, 2H), 4.50 (d, J=10.5 Hz, 1H), 4.56 (d, J=11.7 Hz, 1H), 4.64-4.75 (m, 4H), 4.79 (d, J=11.7 Hz, 1H), 4.80 (d, J=11.4 Hz, 1H), 4.85 (d, J=3.3 Hz, 1H), 4.91 (d, J=11.4 Hz, 1H), 6.10 (d, J=9.0 Hz, 1H), 6.82 (m, 4H), 7.21-7.38 (m, 24H).

Step 2. Preparation of 8-(diheptylamino)-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)octanamide The compound of Step 1 was used in a manner similar to that of Step 2 of Example 1, to afford the object compound as a white wax solid (25 mg, 80%).

¹H NMR (300 MHz, pyridine) δ 0.78-0.88 (m, 9H), 1.17-1.45 (m, 46H), 1.65 (m, 1H), 1.77 (t, J=7.2 Hz, 2H), 1.93 (m, 6H), 2.27 (m, 1H), 2.45 (td, J=7.2, 2.1 Hz, 2H), 3.14 (m, 6H), 4.29-4.68 (m, 10H), 5.24 (m, 1H), 5.56 (d, J=3.9 Hz, 1H), 8.67 (d, J=8.7 Hz, 1H).

Example 15

Preparation of α-Galactosylceramide 17

Step 1. Preparation of N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-11-(dipentylamino)undecanamide The same procedure as in Step 1 of Example 10 was conducted except that 11-dipentylamino-undecanoic acid was used as an acid, followed by silica gel column chromatography eluting with a mixture of 15:1 or 10:1 methylene chloride/methanol to obtain the object compound as a yellow oil (115 mg, 87%).

¹H NMR (300 MHz, CDCl₃) δ 0.91 (t, J=6.6 Hz, 9H), 1.22-1.95 (m, 52H), 2.73 (m, 4H), 3.39-3.53 (m, 3H), 3.67-3.82 (m, 2H), 3.74 (s, 3H), 3.77 (s, 3H), 3.87-4.07 (m, 4H), 4.16 (m, 1H), 4.33 (d, J=8.1 Hz, 1H), 4.36 (d, J=9.0 Hz, 1H), 4.44 (d, J=9.9 Hz, 1H), 4.47 (d, J=10.2 Hz, 1H), 4.50 (d, J=10.8 Hz, 1H), 4.56 (d, J=11.1 Hz, 1H), 4.65 (d, J=12.0 Hz, 1H), 4.67 (d, J=11.1 Hz, 1H), 4.72 (d, J=9.0 Hz, 2H), 4.79 (d, J=9.0 Hz, 1H), 4.80 (d, J=11.7 Hz, 1H), 4.85 (d, J=3.6 Hz, 1H), 4.92 (d, J=11.4 Hz, 1H), 6.07 (d, J=J=8.4 Hz, 1H), 6.82 (m, 4H), 7.21-7.38 (m, 24H).

Step 2. Preparation of N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-(dipentylamino)undecanamide The compound of Step 1 was used in a manner similar to that of Step 2 of Example 1, to afford the object compound as a white wax solid (23 mg, 84%).

¹H NMR (300 MHz, C₅D₅N) δ 0.78-0.87 (m, 9H), 1.18-1.48 (m, 44H), 1.66 (m, 1H), 1.78-1.98 (m, 8H), 2.27 (m, 1H), 2.46 (t, J=7.5, 2H), 3.08 (m, 5H), 4.29-4.69 (m, 10H), 5.27 (m, 1H), 5.57 (d, J=3.9 Hz, 1H), 8.65 (d, J=8.7 Hz, 1H).

Example 16

Preparation of α-Galactosylceramide 18

Step 1. Preparation of N-((2S,3S,4R)-3,4-bis(4-methoxybenzyloxy)-1-((2S,3R,4S,5S)-3,4,5-tris(benzyloxy)-6-(benzyloxymethyl)-tetrahydro-2H-pyran-2-yloxy)octadecan-2-yl)-11-(diheptylamino)undecanamide The same procedure as in Step 1 of Example 10 was conducted except that 11-diheptylamino-undecanoic acid was used as an acid, followed by silica gel column chromatography eluting with a mixture of 15:1 or 10:1 methylene chloride/methanol to obtain the object compound as a yellow oil (98 mg, 89%).

¹H NMR (300 MHz, CDCl₃) δ 0.88 (t, J=6.6 Hz, 9H), 1.22-2.04 (m, 60H), 2.82 (m, 4H), 3.46 (m, 3H), 3.69-3.81 (m, 2H), 3.74 (s, 3H), 3.77 (s, 3H), 3.87-4.07 (m, 4H), 4.16 (m, 1H), 4.33 (d, J=8.4 Hz, 1H), 4.36 (d, J=9.6 Hz, 1H), 4.43 (d, J=10.5 Hz, 1H), 4.47 (d, J=9.9 Hz, 1H), 4.51 (d, J=10.8 Hz, 1H), 4.56 (d, J=11.4 Hz, 1H), 4.63-4.82 (m, 6H), 4.85 (d,

J=3.6 Hz, 1H), 4.91 (d, J=11.4 Hz, 1H), 6.07 (d, J=J=8.4 Hz, 1H), 6.82 (m, 4H), 7.20-7.38 (m, 24H).

Step 2. Preparation of 11-(diheptylamino)-N-((2S, 3S,4R)-3,4-dihydroxy-1-((2S,3R,4S,5S)-3,4,5-trihydroxy-6-(hydroxymethyl)-tetrahydro-2H-pyran-2-yloxy)octadecan-2-yl)undecanamide The compound of Step 1 was used in a manner similar to that of Step 2 of Example 1, to afford the object compound as a white wax solid (27 mg, 87%).

$^1$H NMR (300 MHz, $C_5D_5N$) δ 0.78-0.87 (m, 9H), 1.17-1.45 (m, 52H), 1.65 (m, 1H), 1.75-1.98 (m, 8H), 2.26 (m, 1H), 2.48 (t, J=7.5, 2H), 3.15 (m, 5H), 4.29-4.69 (m, 10H), 5.25 (m, 1H), 5.56 (d, J=3.6 Hz, 1H), 8.65 (d, J=8.7 Hz, 1H).

Example 17

Preparation of α-Galactosylceramide 14

Step 1. Preparation of (13S,14S,15R)-1-bromo-14, 15-bis(4-methoxybenzyloxy)-13-((2S,3R,4S,5S)-3,4, 5-tris(benzyloxy)-6-(benzyloxymethyl)-tetrahydro-2H-pyran-2-yloxy)methyl)nonacosan-11-one The same procedure as in Step 1 of Example 10 was conducted, except that 11-bromo-undecanoic acid was used as the acid, to afford the object compound as a yellow oil (143 mg, 92%).

$^1$H NMR (300 MHz, CDCl$_3$) δ 0.88 (t, J=6.6 Hz, 3H), 1.15-1.60 (m, 38H), 1.78-1.85 (m, 4H), 1.91-1.97 (m, 2H), 3.48 (m, 3H), 3.71 (t, J=4.2 Hz, 1H), 3.75 (s, 3H), 3.77 (s, 3H), 3.81 (dd, J=2.7, 6.9 Hz, 1H), 3.87-4.07 (m, 6H), 4.16 (m, 1H), 4.33 (d, J=11.1 Hz, 1H), 4.37 (d, J=11.7 Hz, 1H), 4.44 (d, J=10.8 Hz, 1H), 4.48 (d, J=11.4 Hz, 1H), 4.51 (d, J=11.1 Hz, 1H), 4.56 (d, J=11.4 Hz, 1H), 4.65 (d, J=11.7 Hz, 1H), 4.68 (d, J=11.1 Hz, 1H), 4.73 (d, J=12.0 Hz, 1H), 4.79 (d, J=11.7 Hz, 2H), 4.86 (d, J=3.6 Hz, 1H), 4.92 (d, J=11.4 Hz, 2H), 6.13 (d, J=8.4 Hz, 1H), 6.79-6.85 (m, 4H), 7.21-7.38 (m, 24H).

Step 2. Preparation of (13S,14S,15R)-1-mercapto-14,15-bis(4-methoxybenzyloxy)-13-((2S,3R,4S,5S)-3,4,5-tris(benzyloxy)-6-(benzyloxymethyl)-tetrahydro-2H-pyran-2-yloxy)methyl)nonacosan-11-one The compound prepared in Step 1 and thiourea (1.5 eq) were added to a dry ethyl alcohol (0.2~0.5 M) solvent and refluxed for 2 hrs. After the addition of 5 N sodium hydroxide thereto, the solution was again refluxed for 2 hrs and then neutralized with 1 N hydrochloric acid. The reaction mixture was diluted with ethylacetate and washed with brine. The ethylacetate layer was dried over magnesium sulfate, concentrated, and purified through silica gel column chromatography (eluent=hexane/ethylacetate, 3:1 or 2:1) to afford the object compound as a colorless oil (120 mg, 80%).

$^1$H NMR (300 MHz, CDCl$_3$) δ 0.88 (t, J=6.5 Hz, 3H), 1.20-1.96 (m, 45H), 2.45 (t, J=7.5 Hz, 1H), 3.46 (m, 4H), 3.71 (m, 1H), 3.75 (s, 3H), 3.77 (s, 3H), 3.80-4.07 (m, 7H), 4.17 (m, 1H), 4.33-4.42 (m, 2H), 4.47 (d, J=9.6 Hz, 1H), 4.51 (d, J=8.7 Hz, 1H), 4.56 (d, J=11.7 Hz, 1H), 4.63-4.71 (m, 2H), 4.75 (d, J=9 Hz, 2H), 4.79 (d, J=11.7 Hz, 1H), 4.85 (d, J=3.6 Hz, 1H), 4.91 (d, J=11.4 Hz, 1H), 6.23 (d, J=7.8 Hz, 1H), 6.82 (m, 4H), 7.20-7.38 (m, 24H).

Step 3. Preparation of N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-mercaptoundecanamide The compound of Step 1 was used in a manner similar to that of Step 2 of Example 1, to afford the object compound as a white wax solid (24 mg, 80%). $^1$H NMR (300 MHz, $C_5D_5N$) δ 0.83 (t, J=6.8 Hz, 3H), 1.11-1.52 (m, 36H), 1.58-1.96 (m, 6H), 2.02-2.29 (m, 2H), 2.56 (t, J=6.9 Hz, 2H), 4.31-4.67 (m, 10H), 5.28 (m, 1H), 5.53 (d, J=2.4 Hz, 1H), 9.10 (d, J=7.8 Hz, 1H).

Example 18

Preparation of α-Galactosylceramide 15

Step 1. Preparation of (14S,15S,16R)-1-bromo-15, 16-bis(4-methoxybenzyloxy)-14-(((2S,3R,4S,5S)-3, 4,5-tris(benzyloxy)-6-(benzyloxymethyl)-tetrahydro-2H-pyran-2-yloxy)methyl)triacontan-12-one The same procedure as in Step 1 of Example 10 was conducted, except that 12-bromo-dodecanoic acid was used as the acid, to afford the object compound as a yellow oil (120 mg, 95%).

$^1$H NMR (300 MHz, CDCl$_3$) δ 0.89 (t, J=6.6 Hz, 3H), 1.14-1.61 (m, 40H), 1.77-1.87 (m, 4H), 1.92-1.97 (m, 2H), 3.48 (m, 3H), 3.72 (t, J=4.2 Hz, 1H), 3.77 (s, 3H), 3.79 (s, 3H), 3.81 (dd, J=2.7, 6.8 Hz, 1H), 3.89-4.10 (m, 6H), 4.15 (m, 1H), 4.33 (d, J=11.2 Hz, 1H), 4.36 (d, J=11.7 Hz, 1H), 4.46 (d, J=10.5 Hz, 1H), 4.47 (d, J=11.6 Hz, 1H), 4.51 (d, J=11.1 Hz, 1H), 4.56 (d, J=11.4 Hz, 1H), 4.66 (d, J=11.7 Hz, 1H), 4.68 (d, J=11.1 Hz, 1H), 4.72 (d, J=11.8 Hz, 1H), 4.80 (d, J=11.7 Hz, 2H), 4.86 (d, J=3.6 Hz, 1H), 4.91 (d, J=11.4 Hz, 2H), 6.14 (d, J=8.4 Hz, 1H), 6.81-6.87 (m, 4H), 7.19-7.37 (m, 24H).

Step 2. Preparation of (14S,15S,16R)-1-mercapto-15,16-bis(4-methoxybenzyloxy)-14-(((2S,3R,4S,5S)-3,4,5-tris(benzyloxy)-6-(benzyloxymethyl)-tetrahydro-2H-pyran-2-yloxy)methyl)triacontan-12-one The compound prepared in Step 1 was used in a manner similar to that of Step 2 of Example 17, to afford the object compound as a colorless oil (110 mg, 77%).

$^1$H NMR (300 MHz, CDCl$_3$) δ 0.86 (t, J=6.6 Hz, 3H), 1.20-1.97 (m, 47H), 2.49 (t, J=7.2 Hz, 1H), 3.46 (m, 4H), 3.71 (m, 1H), 3.75 (s, 3H), 3.77 (s, 3H), 3.80-4.07 (m, 7H), 4.17 (m, 1H), 4.33-4.43 (m, 2H), 4.47 (d, J=9.6 Hz, 1H), 4.51 (d, J=8.7 Hz, 1H), 4.56 (d, J=11.7 Hz, 1H), 4.65 (d, J=11.7 Hz, 1H), 4.68 (d, J=10.8 Hz, 1H), 4.73 (d, J=10.8 Hz, 2H), 4.80 (d, J=11.4 Hz, 1H), 4.85 (d, J=3.6 Hz, 1H), 4.91 (d, J=11.1 Hz, 1H), 6.15 (d, J=8.4 Hz, 1H), 6.82 (m, 4H), 7.21-7.38 (m, 24H).

Step 3. Preparation of N-((2S,3S,4R)-3,4-dihydroxy-1-((2S,3R,4S,5R)-3,4,5-dihydroxy-6-(hydroxymethyl)-tetrahydro-2H-pyran-2-yloxy)octadecan-2-yl)-12-mercaptododecanamide The compound of Step 1 was used in a manner similar to that of Step 2 of Example 1, to afford the object compound as a white wax solid (21 mg, 80%).

$^1$H NMR (300 MHz, $C_5D_5N$) δ 0.84 (t, J=6.8 Hz, 3H), 1.09-1.48 (m, 38H), 1.54-1.96 (m, 6H), 2.04-2.29 (m, 2H), 2.56 (t, J=6.9 Hz, 2H), 4.31-4.66 (m, 10H), 5.26 (m, 1H), 5.53 (d, J=3.0 Hz, 1H), 9.10 (d, J=8.1 Hz, 1H).

Experimental Example 1

Determination of Stimulatory Activity for NKT Hybridoma Cell (Zhou et al., Science, 306:1786-1789, 2004)

Mouse CD1d-bearing rat basophilic leukemia (RBL) cells were incubated with various concentrations of α-GalCer or the α-GalCer derivatives prepared in Examples for 4 hrs. After removing free glycolipids by washing with PBS (phosphate-buffer saline) three times, RBL cells were incubated with DN32.D3 NKT hybridoma cells for 16 hrs. IL-2 secretion levels in the supernatant were determined through ELISA (Enzyme-Linked Immunosorbent Assay).

As shown in FIG. 1, IL-2 production was greatly affected by the length of fatty acid chains. Compounds of Examples 1, 2, 7, 8 and 9, having shorter fatty acid chains, were ineffective for IL-2 production compared to α-GalCer. Derivative 3, having a moderate fatty acid chain, was not active in practice in cytokine production. At high concentrations (100~500 ng/mL), derivatives of Examples 4 to 6, to 12 and 14 to 18 with long fatty acid chains were observed to induce lower levels of IL-2 production than did α-GalCer (FIGS. 1(a) and 1(b)). By contrast, a low concentration of (32 ng/mL) of the derivatives of Examples 5, 11, 12 and 16 showed comparable stimulatory effects to α-GalCer.

Experimental Example 2

Evaluation of Cytokine Levels Produced by Mouse Splenocyte

Splenocytes from naïve C57BL/6 mice were incubated with various concentrations of α-GalCer or α-GalCer derivatives for 72 hrs. IFN-γ and IL-4 secretion levels in the supernatant were determined through ELISA.

Figure 2:
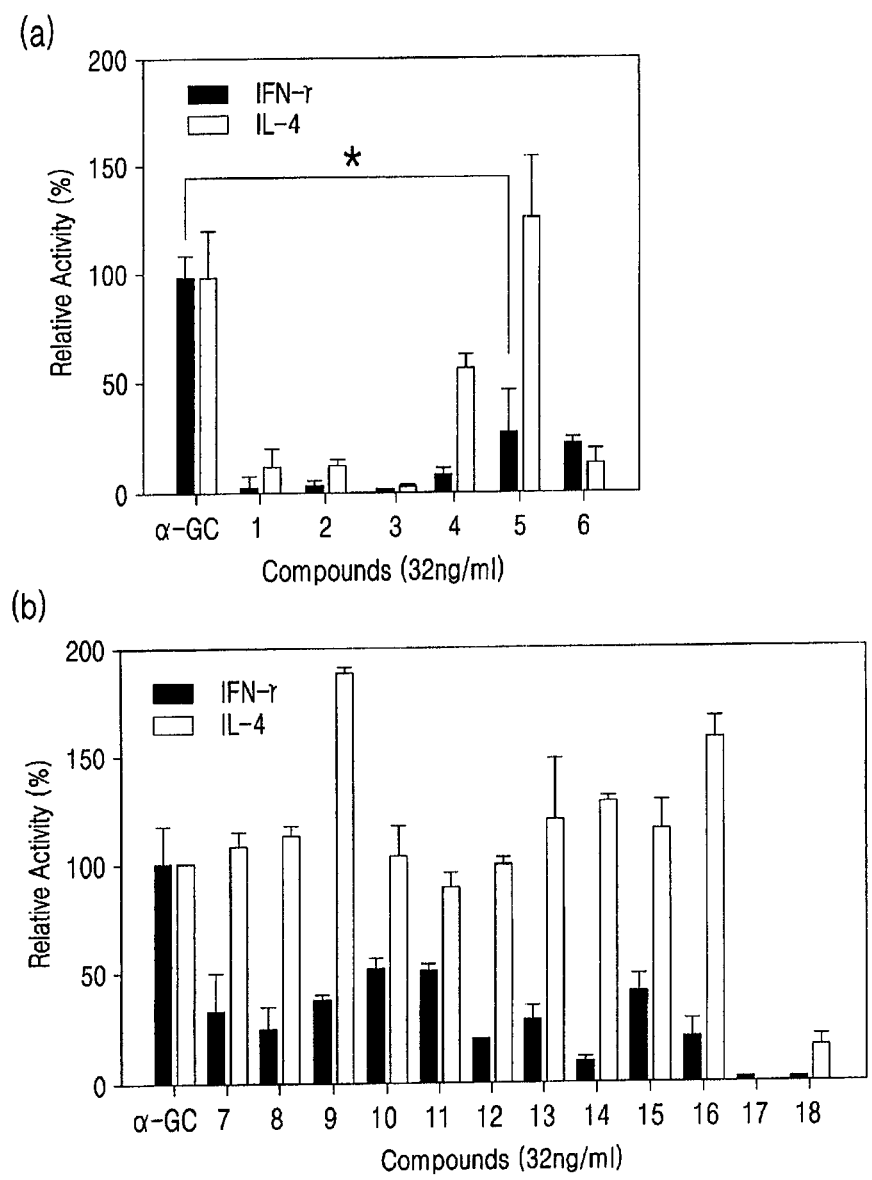
FIG. 2 shows cytokine secretion levels, induced when α-GalCer and the compounds of the present invention are individually used at a concentration of 32 ng/ml.
Figure 3:
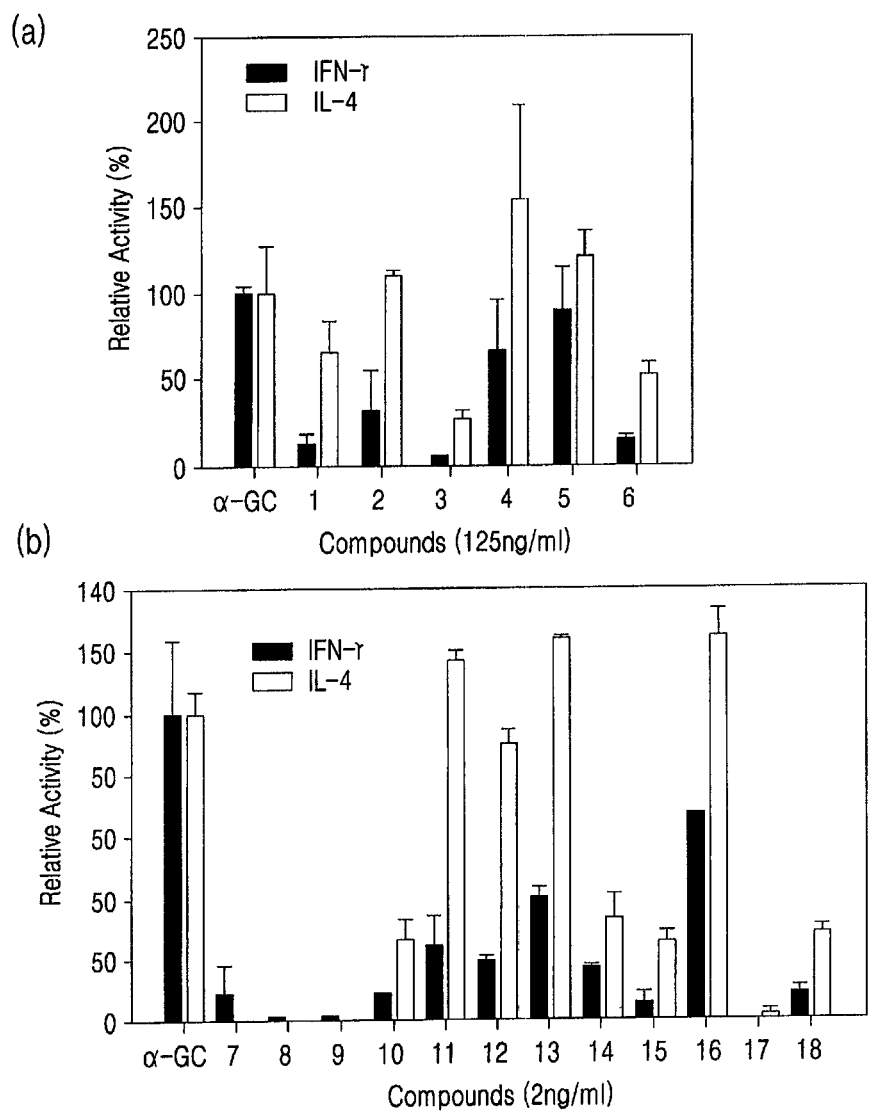
FIG. 3 shows cytokine secretion levels, induced when α-GalCer and the compounds of the present invention are individually used at a concentration of (a) 125 ng/mg and (b) 2 ng/ml.

FIGS. 2 and 3 are graphs showing the levels of the cytokines produced from cells stimulated with α-GalCer or the compounds of the present invention. They show the relative IFN-γ and IL-4 production levels of the compounds of the present invention when compared with those of α-GalCer. The compounds of the present invention were observed to induce a Th2 bias in the NKT cell cytokine responses. At a relatively high concentration (125 ng/mL or 32 ng/ml), the compounds of the present invention were less effective than α-GalCer in IFN-γ production (FIGS. 2(a), 2(b), 3(a) and 3(a)), while compounds of certain Examples (2, 4 and 5) showed equivalent or greater IL-4 secretion than did α-GalCer at high concentrations (125 ng/ml) (FIG. 3(a)). At lower concentrations (32 ng/mL or 2 ng/ml), all derivatives except for the derivatives of Examples 5, 7 and 10 to 18 induced the production of lower levels of IFN-γ and IL-4 than did α-GalCer (FIGS. 2(a) and 2(b)). The derivatives of Examples 11, 13 and 16 induced more IL-4 production compared with α-GalCer (FIG. 3(b)).

Experimental Example 3

Examination of IFN-γ and IL-4 Production Level In Vivo

α-GalCer or the α-GalCer derivatives (1 μg/mouse) were intravenously injected into naïve C57BL/6 mice. The serum concentrations of IFN-γ and IL-4 at each time point were determined through ELISA.

Figure 4:
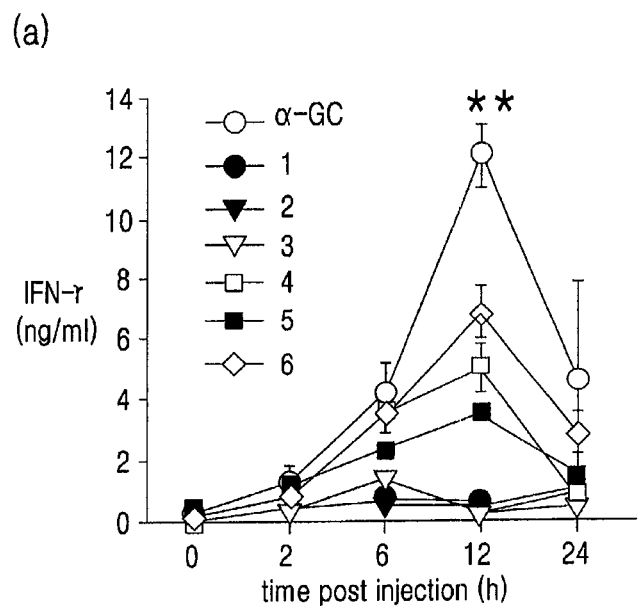
FIG. 4 shows IFN-γ secretion levels induced by α-GalCer and the compounds of the present invention.
Figure 4:
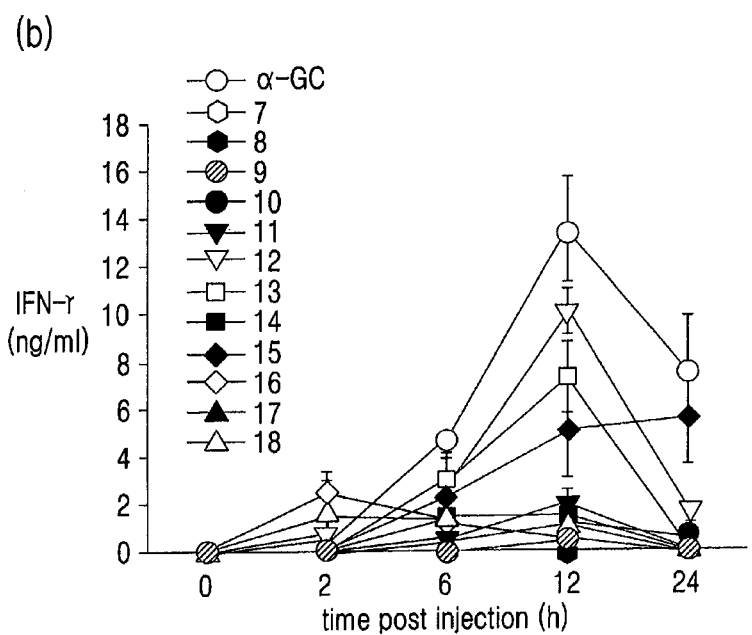
Figure 5:
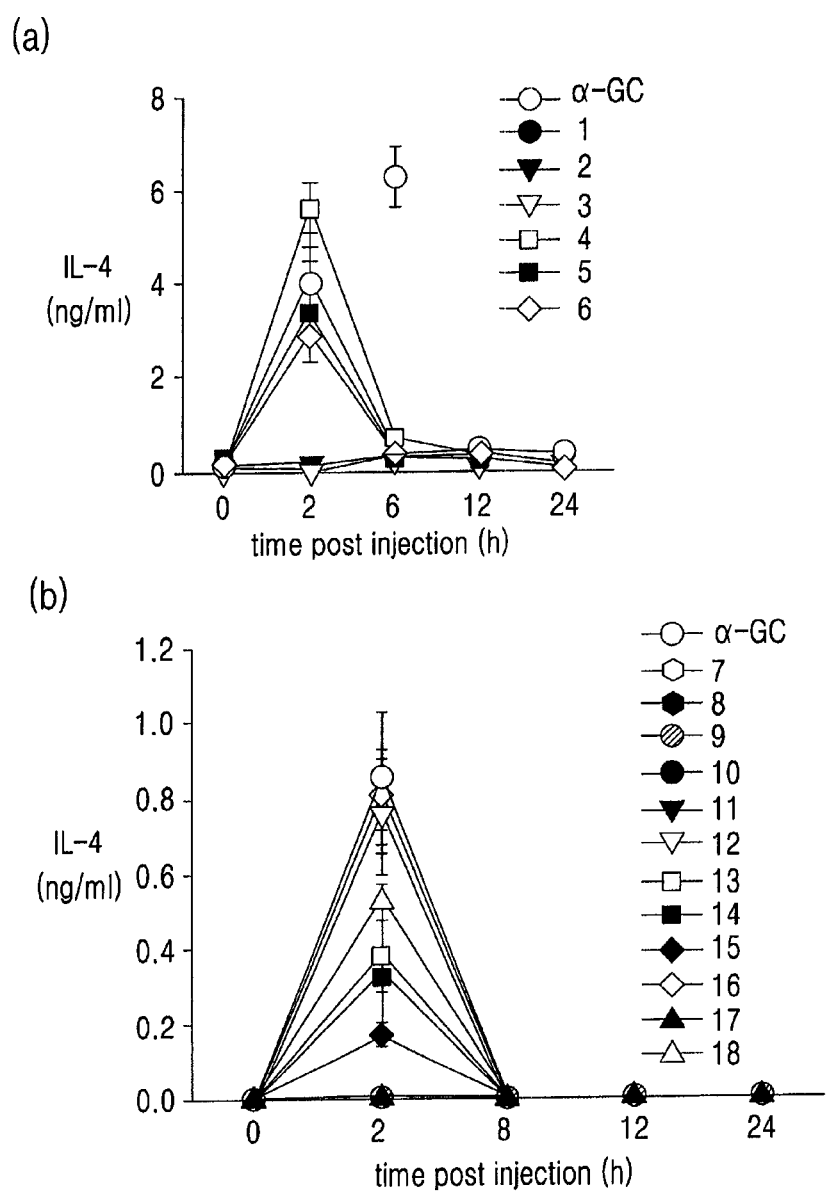
FIG. 5 shows IL-4 secretion levels induced by α-GalCer and the compounds of the present invention.

FIGS. 4 and 5 show the levels of IFN-γ and IL-4 secretion levels upon stimulation with the compounds of the present invention, respectively. In mice administered with α-GalCer or the triazole compounds, IL-4 levels were observed to rapidly increase within 2 hrs after the administration while IFN-γ levels were found to peak 12 hrs after the administration. In animal assays, as shown in FIGS. 4(a) and 4(b), compounds of Examples 1 to 3, 7 to 9 and 16 to 18, which have short or medium fatty acid chains, were observed to be almost non-stimulatory for cytokine secretion, while the compounds of Examples 4 to 6, 12, 13 and 15, which have long chains, provoked relatively small levels of IFN-γ, compared to α-GalCer. In addition, they induced equal or greater IL-4 secretion than α-GalCer, as shown in FIGS. 5(a) and 5(b). Taken together, the data of the in vitro and in vivo experiments show that the long-chain compounds of the present invention have a stimulatory effect on cytokine production comparable to that of α-GalCer. However, their cytokine release profile is somewhat different from the parent α-GalCer. They are observed to bias cytokine secretion toward the Th2 response.

The invention claimed is:

1. An α-galactosylceramide derivative or a pharmaceutically acceptable salt thereof, having the formula:

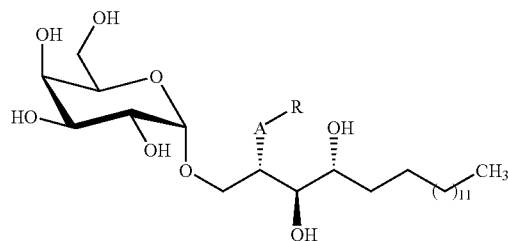

wherein,

A is a triazole group

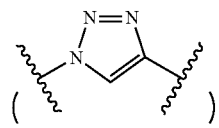

or an amide group

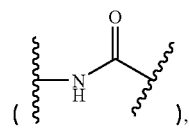

and when A is a triazole group, R is an alkyl group of $C_1$~$C_{35}$ without any substituent, or with at least one substituent, said substituent being halogen, hydroxy, amino, amino having one or more alkyl groups of $C_1$~$C_{20}$, thiol, cyano, nitro, sulfonyl, phenyl, alkoxy of $C_1$~$C_{30}$, alkyl of $C_1$~$C_{30}$, haloalkyl of $C_1$~$C_{30}$, hydroxyalkyl of $C_1$~$C_{30}$, alkoxyalkyl of $C_1$~$C_{30}$, aryl of $C_5$~$C_{10}$, heteroaryl of $C_5$~$C_{10}$, arylalkyl of $C_5$~$C_{10}$ or heteroarylalkyl of $C_5$~$C_{10}$, and when A is an amide group, R is an alkyl group of $C_1~C_{35}$ with at least one substituent, said substituent being amino having two alkyl groups of $C_1~C_{20}$.

2. The α-galactosylceramide derivative or a pharmaceutically acceptable salt thereof, as set forth in claim 1, wherein A is a triazole group or an amide group; and R is an alkyl of $C_1~C_{30}$ without any substituent, or with at least one substituent, when A is a triazole group, said substituent being halogen, hydroxy, amino, amino having one or more alkyl groups of $C_1~C_{15}$, thiol, cyano, nitro, sulfonyl, phenyl, alkoxy of $C_1~C_{20}$, alkyl of $C_1~C_{20}$, haloalkyl of $C_1~C_{20}$, hydroxyalkyl of $C_1~C_{20}$, alkoxyalkyl of $C_1~C_{20}$, aryl of $C_5~C_8$, heteroaryl of $C_5~C_8$, arylalkyl of $C_5~C_8$ or heteroarylalkyl of $C_5~C_8$; or R is an alkyl group of $C_1~C_{30}$ with at least one substituent when A is an amide group, said substituent being amino having two alkyl groups of $C_1~C_{15}$.

3. The α-galactosylceramide derivative or the pharmaceutically acceptable salt thereof as set forth in claim 1, wherein A is a triazole group or an amide group; and R is an alkyl of $C_1~C_{25}$ without any substituent, or with at least one substituent, when A is a triazole group, said substituent being halogen, hydroxy, amino, amino having one or more alkyl groups of $C_1~C_{10}$, thiol, phenyl, alkyl of $C_1~C_{20}$, haloalkyl of $C_1~C_{20}$, or hydroxyalkyl of $C_1~C_{20}$; or R is an alkyl group of $C_1~C_{25}$, with at least one substituent when A is an amide group, said substituent being amino having two alkyl groups of $C_1~C_{10}$.

4. The α-galactosylceramide derivative or the pharmaceutically acceptable salt thereof as set forth in claim 1, wherein A is a triazole group; and R is an alkyl of $C_1~C_{25}$ without any substituent, or with at least one substituent said substituent being phenyl.

5. The α-galactosylceramide derivative or the pharmaceutically acceptable salt thereof as set forth in claim 1, wherein the α-galactosylceramide derivative is selected from a group consisting of:

1) (2S,3R,4S,5R)-2-((2S,3S,4R)-2-(4-hexyl-1H-1,2,3-triazol-1-yl)-3,4-dihydroxyoctadecyloxy)-6-(hydroxymethyl)-tetrahydro-2H-pyrane-3,4,5-triol;

2) (2S,3R,4S,5R)-2-((2S,3S,4R)-2-(4-heptyl-1H-1,2,3-triazol-1-yl)-3,4-dihydroxyoctadecyloxy)-6-(hydroxymethyl)-tetrahydro-2H-pyrane-3,4,5-triol;

3) (2S,3R,4S,5R)-2-((2S,3S,4R)-2-(4-hexadecyl-1H-1,2,3-triazol-1-yl)-3,4-dihydroxyoctadecyloxy)-6-(hydroxymethyl)-tetrahydro-2H-pyrane-3,4,5-triol;

4) (2S,3R,4S,5R)-2-((2S,3S,4R)-3,4-dihydroxy-2-(4-tricosyl-1H-1,2,3-triazol-1-yl)octadecyloxy)-6-(hydroxymethyl)-tetrahydro-2H-pyrane-3,4,5-triol;

5) (2S,3R,4S,5R)-2-((2S,3S,4R)-3,4-dihydroxy-2-(4-tetracosyl-1H-1,2,3-triazol-1-yl)octadecyloxy)-6-(hydroxymethyl)-tetrahydro-2H-pyrane-3,4,5-triol;

6) (2S,3R,4S,5R)-2-((2S,3S,4R)-3,4-dihydroxy-2-(4-pentacosyl-1H-1,2,3-triazol-1-yl)octadecyloxy)-6-(hydroxymethyl)-tetrahydro-2H-pyrane-3,4,5-triol;

7) (2S,3R,4S,5R)-2-((2S,3S,4R)-3,4-dihydroxy-2-(4-(6-phenylhexyl)-1H-1,2,3-triazol-1-yl)octadecyloxy)-6-(hydroxymethyl)-tetrahydro-2H-pyrane-3,4,5-triol;

8) (2S,3R,4S,5R)-2-((2S,3S,4R)-3,4-dihydroxy-2-(4-(7-phenylheptyl)-1H-1,2,3-triazol-1-yl)octadecyloxy)-6-(hydroxymethyl)-tetrahydro-2H-pyrane-3,4,5-triol;

9) (2S,3R,4S,5R)-2-((2S,3S,4R)-3,4-dihydroxy-2-(4-(8-phenyloctyl)-1H-1,2,3-triazol-1-yl)octadecyloxy)-6-(hydroxymethyl)-tetrahydro-2H-pyrane-3,4,5-triol;

10) 8-(diheptylamino)-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)octanamide;

11) N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)-11-(dipentylamino)undecanamide; and 12) 11-(diheptylamino)-N-((2S,3S,4R)-3,4-dihydroxy-1-((2S,3R,4S,5R)-3,4,5-trihydroxy-6-(hydroxymethyl)-tetrahydro-2H-pyran-2-yloxy)octadecan-2-yl)undecanamide.

6. A regulator for cytokine secretion-comprising the α-galactosylceramide derivative of claim 1 or a pharmaceutically acceptable salt thereof as an active ingredient.

7. A pharmaceutical composition for use as an immune adjuvant comprising the α-galactosylceramide derivative of claim 1 or a pharmaceutically acceptable salt thereof as an active ingredient.

8. The pharmaceutical composition according to claim 7, wherein said composition has a therapeutic effect on an interleukin-4 (IL-4) regulated autoimmune disease.

9. The pharmaceutical composition according to claim 7, wherein said composition has a therapeutic effect on type 1 diabetes or multiple sclerosis.

10. The pharmaceutical composition according to claim 7, wherein said composition is suitable to be administrable alone or along with dendritic cells or B cells loaded therewith.

11. An oral or mucosal vaccine comprising the pharmaceutical composition of claim 7.

12. A method for preparing an α-galactosylceramide derivative comprising: a) providing a starting compound having the formula:

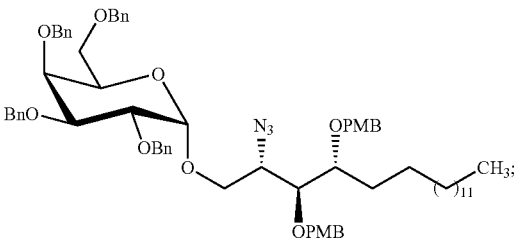

b) reacting said starting compound with an alkyne or carboxylic acid compound selected from the group consisting of

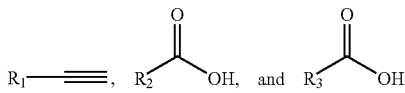

to form an intermediate having the formula:

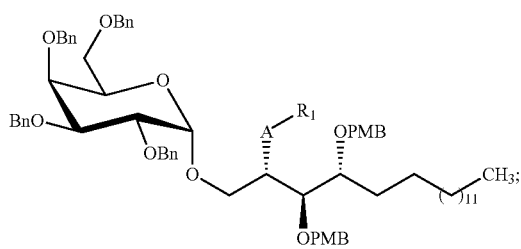

and c) deprotecting the intermediate with Pd(OH)$_2$, wherein,

Bn and PMB represent benzyl and p-methoxybenzyl, respectively, $R_1$ is an alkyl group of $C_1$~$C_{35}$ without any substituent, or with at least one substituent, when A is a triazole group, said substituent being halogen, hydroxy, amino, amino having one or more alkyl groups of $C_1$~$C_{20}$, thiol, cyano, nitro, sulfonyl, phenyl, alkoxy of $C_1$~$C_{30}$, alkyl of $C_1$~$C_{30}$, haloalkyl of $C_1$~$C_{30}$, hydroxyalkyl of $C_1$~$C_{30}$, alkoxyalkyl of $C_1$~$C_{30}$, aryl of $C_5$~$C_{10}$, heteroaryl of $C_5$~$C_{10}$, arylalkyl of $C_5$~$C_{10}$ or heteroarylalkyl of $C_5$~$C_{10}$;

$R_1$ is an alkyl group of $C_1$~$C_{35}$ without any substituent, or with at least one substituent, when A is an amide group, said substituent being amino having two alkyl groups of $C_1$~$C_{20}$;

$R_2$ is a substituent readily convertible to $R_1$, which is protected with a protecting group, and $R_3$ is a substituent readily convertible to $R_1$, which has a leaving group replaceable with a thiourea.

13. A method of treating IL-4-regulated autoimmune diseases comprising administering a pharmaceutical composition, wherein said pharmaceutical composition comprises an α-galactosylceramide derivative or a pharmaceutically acceptable salt thereof having the formula:

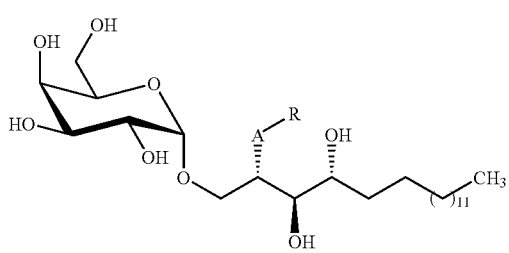

wherein,

A is a triazole group

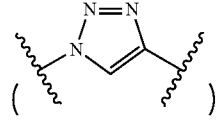

or an amide group

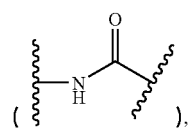

and when A is a triazole group, R is an alkyl group of $C_1$~$C_{35}$ without any substituent, or with at least one substituent, said substituent being halogen, hydroxy, amino, amino having one or more alkyl groups of $C_1$~$C_{20}$, thiol, cyano, nitro, sulfonyl, phenyl, alkoxy of $C_1$~$C_{30}$, alkyl of $C_1$~$C_{30}$, haloalkyl of $C_1$~$C_{30}$, hydroxyalkyl of $C_1$~$C_{30}$, alkoxyalkyl of $C_1$~$C_{30}$, aryl of $C_5$~$C_{10}$, heteroaryl of $C_5$~$C_{10}$, arylalkyl of $C_5$~$C_{10}$ or heteroarylalkyl of $C_5$~$C_{10}$, and when A is an amide group, R is an alkyl group of $C_1$~$C_{35}$ with at least one substituent, said substituent being amino having two alkyl groups of $C_1$~$C_{20}$.

14. The method of claim 13 wherein said pharmaceutical composition is administered in a dose from 1 to 250 μg/day.

15. The method of claim 14 wherein the dose is from 2 to 50 μg/day.

16. The method of claim 12 comprising forming an intermediate having the formula:

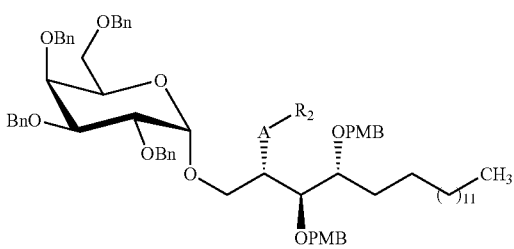

wherein A is a triazole group

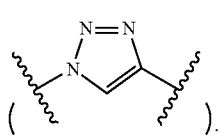

17. The method of claim 12 comprising forming an intermediate having the formula:
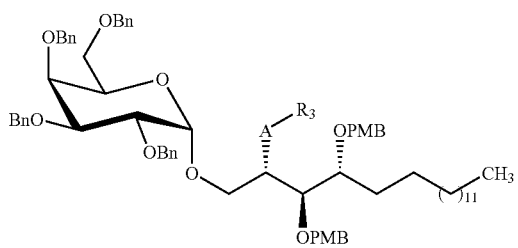
wherein A is an amide group
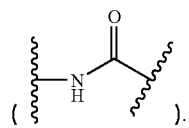
18. The method of claim 12 comprising forming an intermediate having the formula:
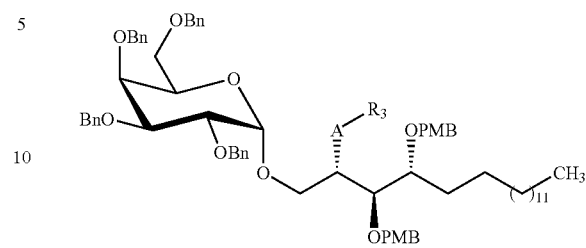
wherein A is an amide group
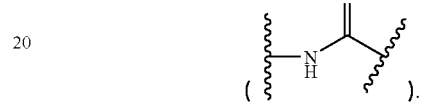
19. The method of claim 18 further comprising reacting the intermediate with a thiourea compound prior to deprotecting the intermediate.
* * * * *